United States Patent [19]

Radhakrishnan

[11] Patent Number: 5,049,389

[45] Date of Patent: * Sep. 17, 1991

[54] NOVEL LIPOSOME COMPOSITION FOR THE TREATMENT OF INTERSTITIAL LUNG DISEASES

[75] Inventor: Ramachandran Radhakrishnan, Fremont, Calif.

[73] Assignee: Liposome Technology, Inc., Menlo Park, Calif.

[*] Notice: The portion of the term of this patent subsequent to Mar. 6, 2007 has been disclaimed.

[21] Appl. No.: 444,738

[22] Filed: Dec. 1, 1989

Related U.S. Application Data

[63] Continuation-in-part of Ser. No. 284,158, Dec. 14, 1988, Pat. No. 4,906,476.

[51] Int. Cl.$^5$ .................... A61K 37/22; A61F 13/00; B01J 13/02
[52] U.S. Cl. .................... 424/450; 424/434; 264/4.1
[58] Field of Search ............ 424/450, 456, 434; 128/200.11, 200.25; 264/4.1

[56] References Cited

U.S. PATENT DOCUMENTS

| | | | |
|---|---|---|---|
| 4,217,344 | 8/1980 | Vanlerberghe et al. | 424/60 |
| 4,484,577 | 11/1984 | Sackner et al. | 128/203.29 |
| 4,649,911 | 3/1987 | Knight et al. | 128/200.21 |
| 4,823,784 | 4/1989 | Bordoni et al. | 128/200.14 |
| 4,849,227 | 7/1989 | Cho | 424/456 |
| 4,897,308 | 1/1990 | Vanlerberghe et al. | 424/450 |
| 4,906,476 | 3/1990 | Radhakrishnan | 424/9 |

FOREIGN PATENT DOCUMENTS

EP87/309854-
.5 9/1988 European Pat. Off. .
WO88/06881 9/1988 PCT Int'l Appl. .
WO88/06882 9/1988 PCT Int'l Appl. .
WO88/06883 9/1988 PCT Int'l Appl. .

OTHER PUBLICATIONS

J. Microencapsulation 4:189–200 (1987), *Inhalation Study Techniques*, pp. 9–31, R. F. Phalen, Editor, CRC Press (1984).
New Eng. J. Med. 315:870 (1986).
Amer. Rev. Resp. Dis. 41:A349 (1988).
Eur. Resp. J. 2:218 (1988).
Eur. J. Resp. Dis. 68:19 (1988).
Biochemistry 17:3759 (1978).
Biochim. Biophsy. Acta 691:227 (1982).

Primary Examiner—Thurman Page
Assistant Examiner—G. S. Kishore
Attorney, Agent, or Firm—Peter J. Dehlinger; Hana Dolezalova

[57] ABSTRACT

A non-conventional lipid particle formulation for the sustained release and delivery of steroids into deep lung is disclosed. The formulation provides prolonged release of the drug, improved therapeutic ratio, lower toxicity, reduced systemic side effects, and stability for several months. The formulation is in particular suitable for treatment of interstitial lung diseases.

28 Claims, 8 Drawing Sheets

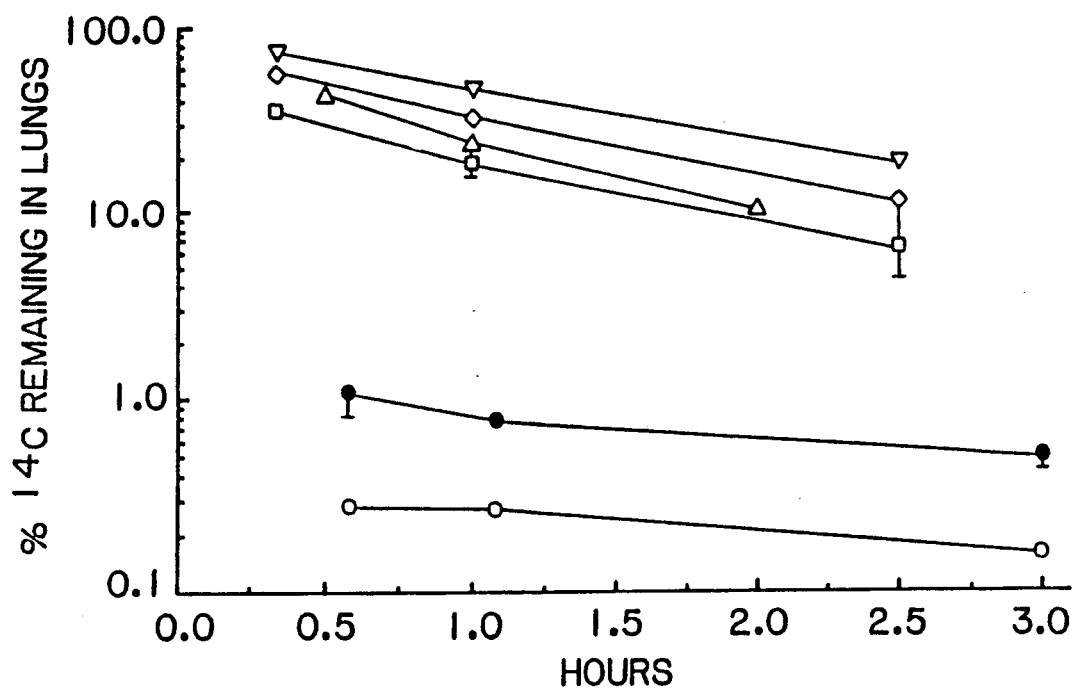

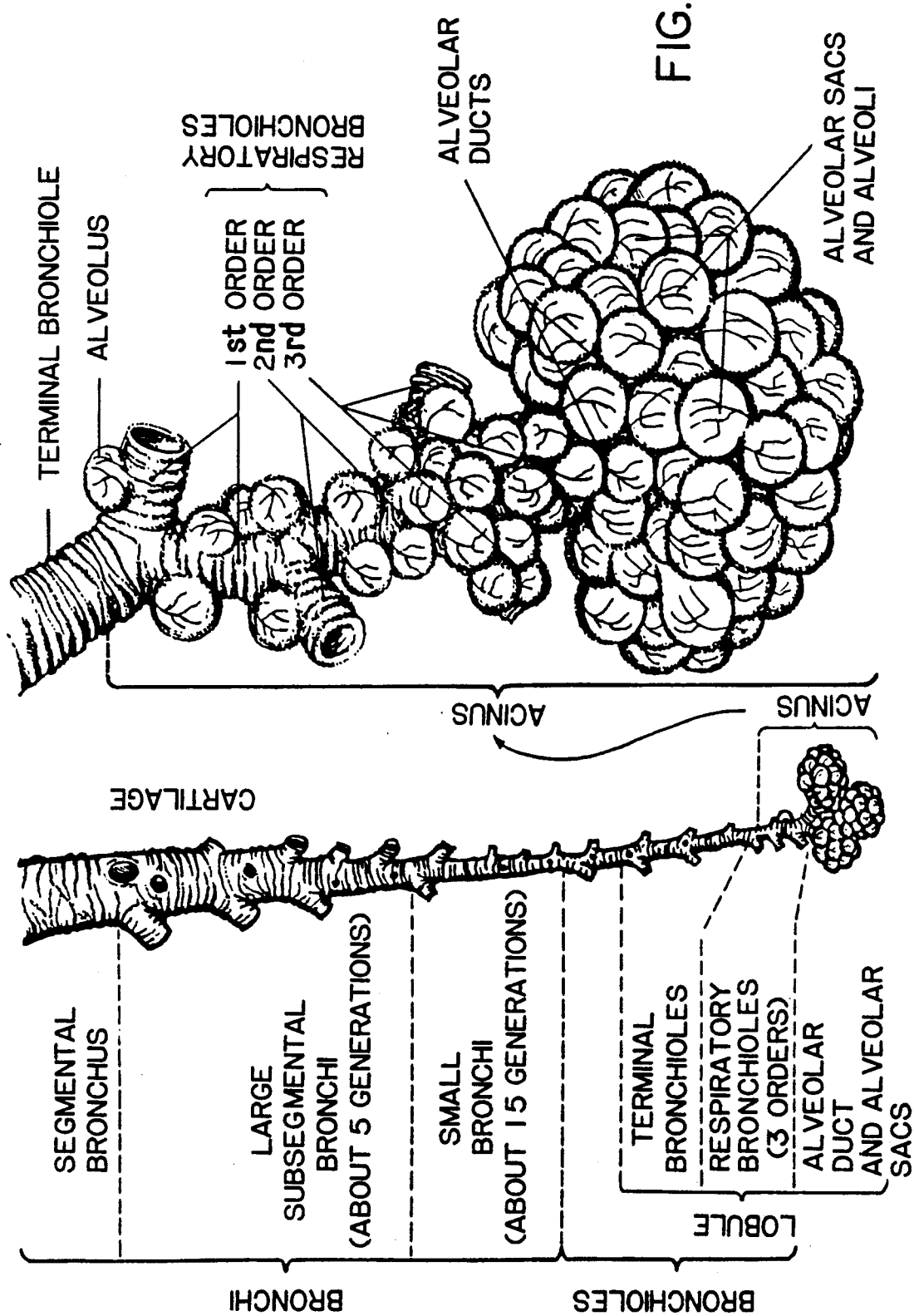

LIPOSOME COMPOSITION FOR THE TREATMENT OF INTERSTITIAL LUNG DISEASES

This is a continuation-in-part application of U.S. patent application entitled "A Novel Liposome Composition for Sustained Release of Steroidal Drugs in Lungs", Ser. No. 284,158, filed on Dec. 14, 1988 and which is now a U.S. Pat. No. 4,906,476 issued on Mar. 6, 1990.

BACKGROUND OF THE INVENTION

1. Field of the Invention

Present invention relates to a novel nonphospholipid liposome composition suitable for treatment of interstitial lung diseases. In particular, the composition provides efficient loading and sustained release of steroidal and other drugs deposited in the deep lung via small size aerosol particles, and is particularly useful in formulating steroids for nebulized inhalation of small aerosol particles.

2. Related Disclosures

Interstitial lung diseases (ILD) are disorders involving lung parenchyma with different etiologies but similar clinical features and diffuse pathologic changes that affect primarily interalveolar interstitial tissue.

Interstitial lung diseases form a heterogeneous group of nearly two hundred diffuse, noninfectious, nonmalignant, inflammatory, and often fatal disorders of the lower respiratory tract, resulting in pathological changes of alveolar tissue, in particular alveolar septum, epithelial and endothelial cells. These diseases progress from the initial acute stage through semichronic to chronic stage and are characterized by progressive development of extensive lung fibrosis or granulomatosis.

In its acute inflammatory phase, interstitial lung diseases are characterized by abnormal accumulation of polymorphonuclear leukocytes, histiocytes, lymphocytes, plasma cells and easinophils with proteinaceous exudate in alveoli and brochioles.

Interstitial lung disorders are caused by a number of agents of various biological origin, such as bacilli, viruses, rickettsiae, mycoplasmas; by agents of physical origin, such as external or internal radiation, oxygen, sulfur dioxide, chlorine or other gases, metal oxide fumes, mercury, toluene, diiosocyanate or other solvent vapors, hydrocarbons, fluorocarbon or chlorocarbon aerosols; by particles such as inorganic dusts, such as asbestos, crystalline silica, silicates, talc, kaolin, aluminum or coal dust; by organic dusts derived from living animal sources such as duck, chicken, bird, or turkey feathers, or mammal fur; or by plant dust such as mushroom, paprika, wheat weevil, wood, coffee and other similar dusts known to cause lung disease. Another source may be various contact chemical agents, such as aspiration of acid, alkali, gastric content or certain therapeutic or diagnostic agents, such as immunosuppressants, chemotherapeutics, antineoplastics, or antibiotics. *Am. J. Med.,* 70:542 (1981).

The acute inflammatory stage usually develops into a subchronic stage characterized by interstitial pneumonia and by initial stages of interstitial pneumonary fibrosis, lymphoid, eosinophilic granuloma, extrinsic allergic alveolitis or sarcoidosis. Hyperplasis of bronchiolar or alveolar epithelium may also be present at this later stage. If the disorder progresses, the exudate may become organized, and necrosis, scarring, and reepithelialization of alveolar septae may take place.

The whole process may ultimately lead to a chronic stage characterized by extensive interstitial fibrosis and, at a later stage of interstitial fibrosis, to a progressive destruction of the lung and formation of cysts, wherein the lungs take on a cystic appearance interspersed with thick bands of fibrotic tissue called honeycomb lung. At this stage, the lung tissue is remodeled and reorganized. The airway alveolar structure is lost and replaced with irregular air spaces with fibrotic walls. *Pathol. Annals,* 21:27 (1986).

Prognosis of these diseases is very poor. Untreated, most interstitial lung diseases are progressive and may rapidly become fatal. The patients' condition deteriorates due to an irreversible loss of alveolar-capillary units. At that stage, the respiratory function is severely impaired, and the right side of the heart becomes hypertrophic due to its attempt to maintain cardiac output and compensate for a progressive loss of alveoli-vascular bed. This eventually leads to the development of cor pulmonale. All the above ultimately result in general respiratory insufficiency with decreased delivery of oxygen to vital tissues such as heart and brain and in death. *Am. J. Med.,* 70:542 (1981).

Two groups of primarily occurring interstitial lung diseases are idiopathic pulmonary fibrosis (IPF) and sarcoidosis. Both idiopathic pulmonary fibrosis and sarcoidosis are, in the first stage, characterized by alveolitis, inflammation of the lung parenchyma.

The clinical course of idiopathic pulmonary fibrosis (IPF) is illustrated in *Chest,* 92:148 (1987). As seen from Table 1 on page 149, almost all patients suffering from IPF die because of respiratory insufficiency or cor pulmonale, with about one-third to one-half patients dying in about five years. The pathogenesis, clinical symptoms and histopathology of the interstitial diseases are illustrated in FIG. 1.

The second most common interstitial lung disease is pulmonary sarcoidosis, a multisystem granulomatous disorder of unknown etiology, characterized histologically by epithelioid granuloma tubercules found usually in lymph nodes, lungs, eyes, liver and skin, but may also appear in spleen, bones, joints, muscle, heart and CNS. The granulomatous tubercles may lead to organ fibrosis, skin, ocular, bronchial, pleural or brain lesions and to many metabolic/hematologic disorders.

Both pulmonary fibrosis or sarcoidosis often lead to respiratory or cardiac failure resulting in death or, alternatively, because of the other symptoms and conditions, result in severe impairment of the quality of the patient's life.

The prevalence of IPF in the United States population is around 0.1 to 0.2% and the prevalence of sarcoidosis is about 0.04%. With the life span of the patient suffering from ILD around five years, an efficient cure would be extremely important and advantageous, particularly since the only effective therapy currently available involves massive doses of steroids.

Conventional therapy of ILD includes systemic administration of multidoses of steroids, in particular corticosteroids or glucocorticoids. Most often used therapy for ILD is 40–80 mg/day of prednisone orally for one to two months. To control symptoms in many ILD chronic cases, a follow-up treatment with lower doses (5–15 mg/day) is needed for weeks, years, or indefinitely. Still, favorable responses to such massive doses of steroids are achieved in only 20–60% of patients.

(*The Merck Manual*, 14th Ed., p. 260 and 685 (1982); *Clin. Geriatr. Med.*, 2:385 (1986); *J. Resp. Dis.*, 10:93 (1989). Moreover, as shown below, massive doses of steroids, while beneficial and tolerable for a short period of time, are accompanied by severe side effects and the benefit of long-term treatment with steroids may be lessened by these undesirable side effects.

Steroids, in particular corticosteroids, have powerful effects on immunologic and hormonal processes and are very effective in treating a wide range of inflammatory diseases, such as arthritis, rheumatoid arthritis, allergic reactions, and conditions such as lung inflammation, alveolitis, asthma, pneumonia and other lung diseases.

As with many potent drugs given systemically, the therapeutic benefits of corticosteroids are accompanied by an array of deleterious side effects, such as muscular atrophy, disruption of adrenal-pituitary axis resulting in stunted growth in children, edema, hypertension, osteoporosis, glaucoma, damage to the immune system leading to susceptibility to viral and fungal infections, psychological disorders, and even heart failure.

Attempts to minimize these complications by administering smaller doses daily or larger doses b.i.d were not very successful. For example, daily systemic administration of smaller, insufficient and inadequate doses of steroids for desired therapy necessitated prolonged treatment. On the other hand, an administration of the higher doses of steroids on alternate days led to peaks of the steroid in the blood level followed by the occurrence of side effects. Both prolonged treatment and side effects were found to be highly undesirable.

Some improvements were achieved by administering steroids via routes that diminish the systemic side effects elsewhere in the body, or by formulating them in delivery systems that might improve the benefit-to-toxicity therapeutic ratio. However, because of poor solubility in water, attempts to formulate steroids in appropriate vehicles for targeted therapies have been generally unsuccessful. Previously used methods for steroid formulation have relied either on use of organic solvents or on crystalline suspensions in an aqueous medium, both of which are prone to cause tissue irritation and may be painful or impossible to administer by certain routes.

To avoid severe systemic side effects, steroids used for treatment of pulmonary conditions may be administered by the inhalation route. Steroidal inhalants are preferred to systemically-administered steroids because they reduce, albeit not eliminate, the side effects. Such reduction is observed even when inhalations are repeated to reach daily recommended doses for treatment of specific pulmonary conditions. However, steroids formulated for inhalation seem to be rapidly absorbed in upper respiratory regions, necessitating frequent dosing, which, in turn, heightens systemic side effects. Very little, if any, of the steroid ends up in alveoli of the lower respiratory region, a primary area affected by the inflammation leading to ILD.

Thus it would be desirable to provide an inhalation formulation which would deliver steroid in sustained time release fashion into the lower lung region.

For successful delivery of steroid into alveoli of the lower pulmonary region, it is important to eliminate from the formulation irritants such as chloroflurocarbons, to decrease the number of required doses, and to provide vehicles that allow deposition of steroid in the alveolar region. Such need can only be met by providing aerosol droplet particles with a mass median aerodynamic diameter of 5 approximately $1-2.1\mu$ size with a geometric standard deviation (GSD) of $1\mu$. Providing sustained controlled release of the steroid from such aerosol would be an added benefit. With the size requirement as outlined above for particle aerosol droplets, presized liposomes of approximately $0.2\mu$ or micelles of particle size of approximately $0.02\mu$, can be used for the generation of aerosol particles that can be deposited in the alveoli in significant amount.

The advantage of inhalation administration of steroids over systemic administration can best be illustrated by a potent anti-inflammatory steroid dexamethasone. Doses of dexamethasone administered systemically by i.v. injection typically range between 0.5 to 9 mg/day. Where, however, dexamethasone is administered via inhalation, the one time dose is approximately 0.084 mg and the corresponding effective daily inhalation dose for dexamethasone is from 0.4 to about 1.0 mg/day. PDR: 1311, 1312 and 1315 (1988).

Beclomethasone, a halogenated synthetic analog of cortisol, faces a similar problem. Beclomethasone dipropionate (BDP) is currently used for oral inhalation and as a nasal spray for treatment of bronchial asthma and seasonal and perennial rhinitis. Because beclomethasone dipropionate is poorly soluble in water, it is currently formulated as a microcrystalline suspension in halogenated alkane propellants, PDR:1003 (1988). Such a formulation is completely unsuitable for treatment of ILD.

The advantages gained with using inhalation rather than a systemic route of administration for treatment of pulmonary diseases are, unfortunately, lessened by the necessity of multiple dosing. Such dosing is inconvenient, unpleasant, and may lead to nasal or oral mucosal tissue damage caused by a repeated use of fluorocarbon propellants, solvents, or other additives necessary for nasal or oral inhalation administration.

Moreover, even with the advantages provided by available inhalation sprays, inhalers, or aerosols for administration of steroids, the requirements for an inhalation formulation suitable for treatment of ILD alveolar inflammation are not met. Since the ILD is a disease of lower respiratory tract, the aerosol droplets carrying the steroid should dominantly be of sizes small enough to reach, enter and be deposited in the alveolar compartment and, to avoid multiple dosing while providing a maximum therapeutic benefit, should also provide a sustained-release of the drug in the alveoli.

Thus, it would be advantageous to have available a steroid composition which is able to carry to and release in the deep lung an effective dose of steroid for extended periods of time, using the minimum amount of steroid. By developing an appropriate formulation vehicle for such therapy, the undesirable side effects accompanying steroid therapy of ILD would be diminished.

Because of their poor solubility in aqueous systems, formulating a steroid in an aqueous solvent requires adding solubilizing agents such as ionic surfactants, cholates, polyethylene glycol (PEG), ethanol, and other solubilizers or using micronized suspension of crystalline drug. While, in general, these agents are considered pharmaceutically acceptable excipients, many of them have, particularly when used for inhalation, have undesirable effects. And since some of these agents are the initial cause of ILD in the first place, their use is doubly imprudent. Therefore, steroid formulations not containing such solubilizing agents and having an aerosol droplets small enough to be able to be deposited in the lung alveoli would be advantageous.

As discussed above, typical treatment of ILD is by oral administration of massive doses of steroids such as 40-80 mg of prednisone/day; 3-9 mg of dexamethasone/day; or 4.8-7.2 mg of betamethasone/day (*Respiratory Pharmacology Therapeutics*, p. 257 (1978). Because of the specific requirements of aerosol droplets of micron or submicron sizes needed for inhalation therapy of the ILD, such therapy has not been until now available. Consequently, the only available data on inhalation therapy are those used for treatment of asthma. A typical daily inhalation dose of dexamethasone for treatment of asthma is 0.75-1 mg/day (PDR, 1312 [1988]). The typical daily inhalation dose of beclomethasone dipropionate for treatment of asthma is 0.25-0.34 mg/day. (PDR, 1315 [1988]).

Several inhalation steroidal products have been introduced recently which are intended for treatment of various pulmonary conditions. For example PULMICORT®, a Freon propelled metered dose (MDI) aerosol of budesonide, delivers 200 ug of steroid per inhalation puff and is available for the treatment of asthma. In limited clinical studies reported in *Amer. Rev. Reso. Dis.* 41:A349 (1988) and in *Eur. Reso. J.*, 2:218 (1988), it was found that the administration of a daily dose of 1200 or 2400 ug of inhaled budesonide via Nebuhaler® showed improvement in chronic relapsing Stage II and III pulmonary sarcoidosis. There are two primary disadvantages connected with the PULMICORT treatment. First, to reach a rather high daily dose of 1.2-2.4 mg, multiple dosing is required which is not desirable in case of lung inflammation. Second, MDI is propelled by a fluorocarbon which alone may be an initial stimulus causing the acute alveolitis. Third, the MDI does not provide particles small enough to enter the alveoli without added spacers or other equipment (*Eur. J. Reso. Dis.*, 68:19 [1988]).

NASALIDE®, a commercially available nasal spray containing steroid flunisolide is used primarily as a local topical treatment for allergic rhinitis. The dose required for treatment of asthma is between 1-2 mg and can only be lo delivered in 250 ug/puff. Consequently, several doses per day is needed.

Still another steroidal formulation used for treatment of bronchial asthma by nebulization is a suspension of beclomethasone dipropionate in an aqueous medium (BECOTIDE®). This suspension has only 50 ug/ml of the active ingredient and has very poor, if any, alveolar deposition. Based on maximum formulable BDP (50 ug/ml) in aqueous medium, it does not provide a sufficient therapeutic amount of steroid to treat sarcoidosis or IPF.

Thus it would be highly desirable to have available a steroidal formulation suitable for inhalation which would provide small, substantially homogeneous size particles allowing the steroid to be deposited in the alveoli.

Certain improvements have previously been achieved by encapsulating steroids in conventional liposomes. For example, smaller doses of steroids were found to be effective when administered in liposome-encapsulated form. Also, modest prolongation of effect and restriction of the drug to the site of administration was achieved, and a marginal degree of decreased rate of systemic uptake was accomplished.

Liposomes, lipid based drug carrier vesicles, are composed of nontoxic, biodegradable lipids, in particular phospholipids which act the same as surfactant in the lung. Attempts have been made to prepare liposomes from nonphospholipid components which have the potential to form lipid bilayers (*Biochim. Biophys. Acta.* 19:227-232 [1982]). Currently, both conventional and nonphospholipid liposomes are rapidly becoming accepted as pharmaceutical agents which improve the therapeutic value of a wide variety of compounds. Liposome drug delivery systems are reviewed in detail in *Cancer Res.*, 43:4730 (1983).

Liposomes generally have been known to improve formulation feasibility for drugs, provide sustained release of drugs, reduce toxicity and side effects, improve the therapeutic ratio, prolong the therapeutic effect after each administration, reduce the need for frequent administration, and reduce the amount of drug needed and/or absorbed by the mucosal or other tissue.

The use of liposomes as a solubilizing agent for steroids in aqueous, nebulized inhalation suspensions essentially eliminates the use of potentially toxic halogenated hydrocarbon propellants and other solvents, and ensures that the drug stays in a stable suspension. Liposome formulation also prevents the lung irritation caused by drug sedimentation and crystallization often encountered with conventional steroidal suspension preparations.

Notwithstanding the above, utilizing conventional liposomes for inhalation formulations still entails some problems. First, there is a little effect of liposomal entrapment on rapid systemic uptake, indicating that even from the liposomes the steroid is rapidly released. Second, because of their poor formulation properties, many useful steroids must be derivatized or modified to be accommodated within the chemical structure of the liposomes for enhanced retention. For example, a 6-18 carbon-chain ester needs to be present in the steroid molecule for optimal lipophilic interaction between the water-insoluble corticosteroid and the lipid membrane.

The necessity for steroid modification is addressed in EPO application 850222.2, which describes increased binding of the steroid to the liposomal membrane by derivatizing said steroid with a hydrophobic anchor, such as a fatty acyl chain. While the binding of derivatized drug to the membrane was shown to be improved, the steroid derivative still did not sufficiently slow the efflux rates of steroid from liposomes. This was due to the fact that the lipid composition of conventional, phospholipid liposomes does not provide a strong enough barrier to slow down the release of the derivatized steroid and to achieve prolonged release.

U.S. Pat. No. 4,693,999 discloses new steroid derivatives obtained by modification of corticosteroids with fatty acid esters which, when incorporated in the lipid portion of liposomes for delivery via inhalation, provide a prolonged steroid retention in the respiratory tract of experimental animals.

Dexamethasone palmitate, a modified synthetic analog of cortisol, incorporated in liposomes was shown to surpass the effectiveness of microcrystalline cortisol acetate injection into arthritic joints of experimental animals. *J. Microencapsulation*, 4:189-200 (1987). While the formulation provided enhanced therapy against inflammation and diminished the leakage levels of the steroid into systemic circulation, it was not therapeutically suitable because the charged carrier dicetyl phosfhate, necessary for the liposome formulation, is not pharmaceutically acceptable for certain safety reasons.

It will be appreciated that designing and synthesizing new steroid derivatives is inconvenient, costly, slow, laborious, and most importantly, often changes the drug efficacy. Thus, it would be greatly advantageous to provide a liposomal steroid formulation with substantially improved drug retention without the need for drug modification.

Poorly water-soluble steroids are generally also difficult to load into conventional phospholipid liposomes because they tend to crystallize rather than incorporate into the phospholipid liposomal membrane. Thus, they have similar toxicity upon administration as do non-liposomal steroidal suspensions since these synthetic drugs do not have the right stearic fit in the bilayer matrix of liposomes, the drugs rapidly diffuse out in vivo.

Previously disclosed (EP 87309854.5) small particle aerosol liposomes and liposome-drug combinations for medical use tried to circumvent but fell short of the strict size requirement for delivery of steroid into alveoli. With aerosol particle size requirement for deposition in alveoli around 1-2.1 $\mu$ MMAD, the size of aerosol droplet delivering drug into alveoli must be substantially within that size limit, preferably with the majority of single aerosol droplet about or smaller than 2 $\mu$ for optimal alveolar deposition. The above cited reference attempted processing a heterogeneous size (1-10 $\mu$) population of liposomes into a more homogeneous size of small liposomes using an aerosol nebulizer equipped to reduce the size of liposomes. In this manner, the majority of resulting aerosol particles were less than 5 $\mu$ in diameter with an aerodynamic mass median diameter ranging from about 1-3 microns. Although some of these particles may reach alveoli, a sizable fraction is far too large to be able to enter the small alveoli and consequently, the drug payload in deep lung could be therapeutically insignificant. Also, because of the sizing by aerosolization, the size distribution of these liposomes is unpredictable and the amount of drug deposited in the deep lung cannot be even estimated, not to say predicted, with any degree of certainty.

Previously available conventional liposomal steroidal formulations have shown an uncontrollable and fast release rate. Measurements of systemic uptake from the respiratory tract after inhalation of underivatized steroids formulated in conventional liposomes indicated little or no effect of liposomal entrapment on the release rate. This means that despite the liposome-binding, the drug was still released relatively quickly from the conventional phospholipid liposomes. This may be due to the fact that all synthetic steroids which are lipophilic tend to be released from the lipid membrane faster than water-soluble drugs encapsulated inside the liposomes because of incompatible stearic fit. *Biochem. J.* 158:473 (1976).

To provide effective treatment for interstitial lung diseases, it would be greatly desirable to develop a pharmaceutically acceptable composition suitable for inhalation administration where the steroids could be formulated without the need of modifying or derivatizing, which at the same time could carry a sufficient amount of steroid and from which the steroid could be released with a controllable and desired rate in nebulized aerosol droplets of small and homogeneous size. The resulting composition would be capable of (a) solubilizing the underivatized steroid, (b) having high-loading ability, (c) prolonging release, (d) extended stability and (e) being deposited in deep lung tissue.

It is the primary object of this invention to provide the liposome-steroid composition wherein the poorly water soluble or insoluble, sedimentation-prone, underivatized or unmodified steroids are successfully sequestered within the membrane of liposomal lipid vesicles of homogeneous and controllable particle size of 0.2-0.5 $\mu$, having at the same time high encapsulation values, long-term stability, and effective sustained release of the drug. The resulting composition would allow an administration of low doses of steroid thus reducing or eliminating toxicity and systemic side effects while at the same time providing pharmacologically bioavailable doses of steroid in deep lung alveoli. The composition would also be economically advantageous because it would effectively formulate all therapeutically needed steroids without loss occurring during the steroid formulation or during the therapeutical administration.

SUMMARY

One aspect of this invention is to provide a nonphospholipid, cholesterol/cholesterol ester salt/steroid liposome formulation for therapeutic delivery of various underivatized and unmodified steroid drug in the liposome vesicles of uniform and controllable particle size in nebulized form into the deep lung tissue.

Other aspect of this invention is to provide a formulation enabling liposome entrapment or encapsulation of underivatized steroids in the liposome vesicles of uniform and controllable particle size suitable for delivery of steroid to alveoli.

Still another aspect of this invention is to provide a liposome formulation with high encapsulation properties for encapsulating water-insoluble steroids or other drugs suitable for aerosolization.

Yet another aspect of this invention is to provide liposome/drug compositions which has lower toxicity, lower side effects, allows the targeting to and release of steroid in a deep lung tissue, removes need for multiple dosing, can be sterilized, and is sufficiently stable in dried form for long-term storage.

Another aspect of this invention is to provide controlled, sustained release in the deep lung of the steroidal drugs or other from the nonconventional liposome/steroid composition.

Still another aspect is to provide a process for making novel nonconventional liposome compositions for controlled release of steroidal or other drugs delivered by nebulization.

Yet another aspect of this invention is to provide the method of treatment of interstitial lung diseases by administering the nebulized liposomal drug composition by oral inhalation.

BRIEF DESCRIPTION OF DRAWINGS

FIG. 7 shows the amounts of radiolabeled BDP remaining in the rat lungs following intratracheal instillation of five different liposome-encapsulated BDP formulations and the amount of the radiolabeled BDP in the lungs found after the intravenous administration of the free BDP.

FIG. 8 depicts pulmonary anatomy showing the division of one larger bronchus into smaller bronchi, which divide into bronchioli, which divide into terminal bronchioles, respiratory bronchioles, alveolar ducts, sacks, and ultimately into individual alveoli.

DETAILED DISCLOSURE OF THE INVENTION

Figure 1:
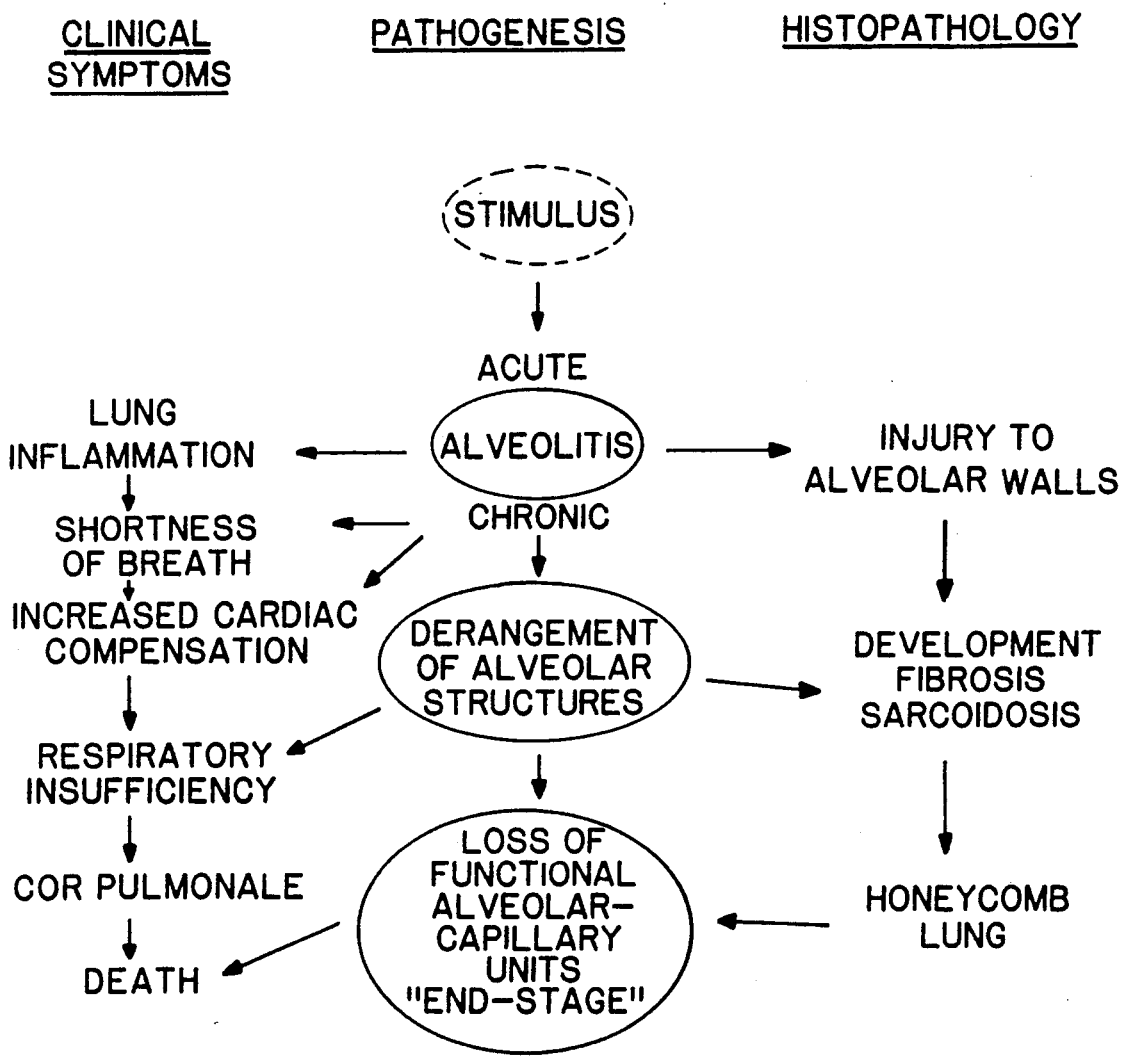
FIG. 1 depicts the current concept of pathogenesis, clinical symptoms and pathological changes connected with interstitial lung disease.

According to the present invention, it has been discovered that beclomethasone dipropionate, other steroids in modified or underivatized form and other nonsteroidal drugs may be successfully retained in nonconventional liposomes for sustained release in deep lung tissue when the liposomes are formulated to contain a mixture of cholesterol and cholesterol ester salt such as sodium cholesterol sulfate. Sodium cholesterol sulfate or other cholesterol ester salts act as a temporary barrier against drug efflux from the liposomes. To design the optimal formulation for high drug loading and sustained release of underivatized steroid, a number of different formulations were developed, studied, and compared with compositions comprising components of the invention in various amounts and ratios as well as conventional phospholipid liposomes derived from egg, soybean, and synthetic phospholipids.

Methods of Liposome Formation

The liposome suspension of the invention can be prepared by any of the standard methods for preparing and sizing liposomes. These include hydration of lipid films, solvent injection, reverse-phase evaporation and other methods, such as those detailed in *Ann. Rev. Biophys. Bioeng.* 9:467 (1980). Reverse-phase evaporation vesicles (REVs) prepared by the reverse-evaporation phase method is described in U.S. Pat. No. 4,235,871, incorporated hereby by reference. The preparation of multilamellar vesicles (MLVs) by thin-film processing of a lipid film or by injection technique is described in U.S. Pat. No. 4,737,923, incorporated by reference. In the two later procedures, which are generally preferred, a mixture of liposome-forming lipids dissolved in a suitable solvent is evaporated in a vessel to form a thin film, which is covered by an aqueous buffer solution. The lipid film hydrates to form MLVs, typically with sizes between about 0.1 to 10 microns.

The REVs or MLVs are further treated to produce a suspension of smaller, substantially homogeneous liposomes, in the 0.02-2.0 micron size range preferably in 0.2-0.4 $\mu$ range. One effective sizing method involves extruding an aqueous suspension of the liposomes through a polycarbonate membrane having a selected uniform pore size, typically 0.2 $\mu$. *Ann. Rev. Biophys. Bioeng.*, 9:467 (1980). The pore size of the membrane corresponds roughly to the largest sizes of liposomes produced by extrusion through that membrane, particularly in which the preparation is extruded two or more times through the same membrane. A more recent method involves extrusion through an asymmetric ceramic filter. The method is detailed in U.S. Pat. No. 4,737,323, incorporated hereby by reference.

Alternatively, the REVs or MLVs can be treated by sonication to produce small unilamellar vesicles (SUVs) which are characterized by sizes 0.02-0.07 $\mu$. Because of the small particle sizes, SUVs are particularly suitable for the delivery of steroid to the alveoli. Another advantage of SUVs is the greater packing density of liposomes at a mucosal surface, thus making SUVs preferable for inhalation for treatment of deep lung diseases such as idiopathic infiltrative pulmonary fibrosis, degenerative interstitial pneumonias and sarcoidosis.

The use of all types of liposomes such as SUVs, MLVs, OLVs or mixtures thereof is contemplated, provided they can be nebulized into aerosol particles suitable for therapeutic administration to deep lung.

One preferred method for producing SUVs is by homogenizing MLVs, using a conventional high pressure homogenizer of the type used commercially for milk homogenization. Here the MLVs are cycled through the homogenizer, with periodic sampling of particle sizes to determine when the MLVs have been substantially converted to SUVs.

The drug is encapsulated in the liposomes by using for example the procedure described in U.S. Pat. No. 4,752,425, incorporated by reference.

Conventional and Nonconventional Liposomes

As defined herein "the conventional liposomes" mean liposomes which contain phospholipids, and the "nonconventional liposomes" mean liposomes which do not contain phospholipids but are formed solely by cholesterol and cholesterol derivatives or, alternatively by amphipathic lipid components. "Cholesterol derivatives" as used herein mean cholesterol esters and salts thereof, "cholesterol salt" means a salt of cholesterol ester and "cholesterol sulfate" means a salt, preferably sodium of cholesterol sulfate. Both conventional and nonconventional liposomes can be formed by a variety of standard methods from a variety of vesicle-forming lipids. For the conventional liposomes these lipids include dialiphatic chain lipids, such as phospholipids, diglycerides, dialiphatic glycolipids, and cholesterol and derivatives thereof. The various lipid components are present in an amount between about 40–99 mole % preferably 60–90 mole % of the total lipid components in the liposomes; cholesterol or cholesterol derivatives are present in amounts between 0–40 mole %. In the nonconventional liposomes the cholesterol derivatives are present in amounts between 30–70/20–50/0.01–20 mole % of cholesterol ester salt to cholesterol to drug, respectively. The drug encapsulated in both kinds of liposomes is in amounts of 0.01–20 mole %.

As defined herein, "phospholipids" include but are not limited to phosphatidic acid (PA) and phosphatidyl glycerol (PG), phosphatidylcholine (PC), egg phosphatidylcholine (EPC), lysophosphatidylcholine (LPC), phosphatidylethanolamine (PE), phosphatidylinositol (PI), and phosphatidylserine (PS). These phospholipids may be fully saturated or partially saturated. They may be naturally occurring or synthetic.

The liposome composition may be formulated to include minor amounts of fatty alcohols, fatty acids, and/or cholesterol esters or any other pharmaceutically acceptable excipients with the proviso that these minor lipid components do not significantly reduce the binding affinity of the liposomes for mucosal or lung tissue, are substantially unsaturated, are not toxic or irritating and do not alter the release properties of the drug.

Preparation of Nonconventional Liposome Composition

According to the present invention, it has been discovered that beclomethasone dipropionate (BDP) or other steroids in underivatized form may be successfully retained in liposomes for delayed release when the liposomes are formulated to contain a high percentage of cholesterol ester salt, such as sodium cholesterol sulfate, typically from 30-70 mole %, preferably 50 mole % and, in combination with cholesterol, typically from 20-50 mole %.

According to one aspect of the invention, it has been discovered that the underivatized drug/cholesterol/cholesterol sulfate composition of the invention has much improved properties such as lesser toxicity, decreased side effects, controllable sustained release, improved solubility, high encapsulation, steroid release at the target organ, absence of need for multiple dosing, extended stability in that it can be stored long-term in dried form without significant increase in particle size on rehydration, and may be nebulized to provide a homogeneous mixture of aerosol particles having mass median aerodynamic diameter smaller than 2.1 μm and preferably smaller than 1 μm. It is believed that aerosol droplets having particle sizes of MMAD larger than 3 μm will only reach secondary bronchi and will not be useful in alveolar processes. On the other hand, particles with size of 2 μm or smaller MMAD have the probability of reaching terminal bronchi/alveolar border at the upper end of the droplet size.

To achieve all the above advantages, the current invention combines the lipid components including cholesterol with cholesterol ester salt, preferably sodium cholesterol sulfate, providing the hydrophilic group, and the steroidal or other drug to be formulated to provide a novel, highly efficient nonconventional liposomal composition for formulation of natural or synthetic underivatized steroids or other drugs. The composition is engineered for increased drug loading and a controllable sustained release rate of the drug in the deep lung tissue. It also provides a means to solubilize the steroids and incorporate them in such liposomal composition without need to modify the drug. Further, the formulation can be easily sterilized thus meeting an important requirement for pharmaceutical preparations. I is also stable and suitable for long-term storage.

In a practice of this invention, lipid bilayers consisting entirely of cholesterol in their hydrophobic core can be conveniently constructed if a hydrophilic group is built in as part of the steroid molecule. Sodium salt such as sodium cholesterol sulfate was used to provide such a hydrophilic group. With equimolar amounts of cholesterol added to the cholesterol sulfate, multilamellar liposomes are initially formed with brief sonication which on prolonged sonication become unilamellar liposomes. The resulting nonconventional liposomal vesicles are comparable in suspensions to those of conventional (phospholipid) vesicles in all aspects. Since cholesterol of nonconventional liposomes bilayers possess internal barriers that are less easily permeated, they allow controllable sustained release of steroidal or other drug from the core. These nonphospholipid bilayers can keep drugs in particular steroid by hydrophobic and electrostatic interactions in bilayer leaflet thus providing slow release making these liposomes superior to phospholipid liposomes.

The composition of the current invention comprises a lipid component, such as cholesterol ester salt, cholesterol, and drug in a ratio from 30-70:20-50:0.1-20 mole %. The best suited liposomal formulations for sustained release of the steroids and other drugs were found to be sodium cholesterol sulfate:cholesterol:steroid in mole % ratio of 55:40:5; 50:40:10; 53:37:9, and most preferably 50:40:10 mole %.

Nonphospholipid liposome compositions containing steroids may further contain any suitable pharmaceutically acceptable additive, diluent and or/excipient. Examples of such additives, diluents or excipients, such as sodium or potassium chloride, mono or dibasic sodium phosphates in hydrated or dehydrated form, water, saline, etc., are not intended to limit the scope of this invention and may be used in any amount needed or necessary which is pharmaceutically acceptable for inhalation formulations.

Table II illustrates the quantitative composition of the optimal BPD-liposome composition for inhalation.

A lipid composition containing sodium cholesterol sulfate: cholesterol:BDP, at a mole ratio of 50:40:10 had the best delayed release of the drug when administered to animals by way of instillation in the respiratory tract, and by inhalation of aerosolized or nebulized liposome particles.

All pharmaceutically acceptable cholesterol ester salts and excipients can be used in the formulation. While sodium cholesterol sulfate is preferred, the composition is not restricted to this particular salt and any other suitable cholesterol ester such as cholesterol nitrate, maleate, phosphate, acetate, and others esters can be advantageously used. In addition, the cholesterol sulfate sodium salt may be converted to other salts with different cations, which may include potassium. lithium, magnesium, calcium and other divalent cations, tris, triethanolamine, ethanolamine, heterocycles and such other salts commonly used and pharmaceutically acceptable in pharmaceutical formulations.

Buffer used in the preparation of the nonconventional liposomes may be any buffer chosen from the group of citrate, carbonate, bicarbonate, acetate, Tris. glycinate, cacodylate, maleate, and such other, and preferably phosphate buffered saline of pH 7.4.

Any organic solvent such as lower alcohols, dimethoxyethane, dioxane, tetrahydrofuran, tetrahydropyran, diethylether, acetone, dimethylsulfoxide (DMSO), dimethylformamides (DMF), and halogenated hydrocarbons, such as Freon, acetonitrile, or mixtures thereof, preferably chloroform/ methanol are used in the process of generation of liposomes.

The method of preparation of nonconventional liposomes comprises:

(1) mixing cholesterol, cholesterol ester salt, preferably sodium cholesterol sulfate, and steroidal drug in dry form, in amounts from 20-50 mole % of cholesterol, 30-70 mole % of cholesterol salt and 0.1-20 mole % of steroid, preferably 40 mole % of cholesterol, 50 mole % of sodium cholesterol sulfate and 10 mole % of a drug;

(2) dissolving the mixture in 5-30 ml of an organic solvent, preferably in 10 ml of methanol:chloroform (2:1 v/v);

(3) repeatedly drying obtained solution under nitrogen and/or vacuum, preferably three times or until the dried film forms on the bottom of the flask and/or, lyophilizing the dry film for 10-180 minutes, preferably for 30 minutes, at temperatures of 18° C.–27° C., preferably at room temperature;

(4) resuspending the residue in 1–10 ml of buffer at pH 7.2–7.6 preferably in the phosphate-buffered saline, pH 7.4;

(5) forming the liposomes by sonication, solvent injection or any other suitable method;

(6) sizing the liposomes by extrusion, or by other methods; and (7) sterilizing the liposomes using the methods described above or any other method suitable and acceptable for sterilization of liposome formulations.

Methods of preparing the composition of the invention are not limited to those named above, but all methods of liposome preparation such as solvent injection, thin film hydration, dehydration-rehydration, and reverse evaporation are equally suitable.

Encapsulation Values

Drug encapsulation means the amount of the drug incorporated, loaded, associated, bound or otherwise attached to the liposomes or their bilayers. In general, the ability of liposomes to encapsulate drug is expressed in % of the drug's starting amount. Thus, the optimal encapsulation percentage 100% is achieved where all drug is encapsulated in liposomes. Technically, however, it is often difficult to achieve 100% encapsulation because the encapsulation % depends on the lipid properties, on the drug properties and on the encapsulating method used.

The primary advantage of nonconventional liposomes is their high encapsulation value in particular for steroids. The nonconventional cholesterol sulfate liposomes demonstrate exceptionally high drug loading with encapsulation values up to 100%, when around 10 mole % drug is used with total lipid concentration of around 40 μ mol/ml, compared with conventional phospholipid liposomes, which generally allow only about 1–3 mole percent drug encapsulation at a total lipid concentration of 40 umol/ml. For example, unsaturated conventional liposomes without cholesterol have a low encapsulation value with the flexibility of accommodating only 1–3 mole percent of steroidal drug. Saturated conventional liposomes composed of lipid such as fully hydrogenated soy PC do not accommodate even small amounts of the steroidal drug. Even though liposomes containing lyso-PC can accommodate a certain amount of steroid to fill in the acyl chain vacancy, such lyso-PC liposomes containing even as little as 2 mole percent of the steroidal drug exchange and release their drug readily, defeating the whole purpose of drug encapsulation in liposomes (Table I). Encapsulation of steroids into conventional liposomes are thus difficult and a large amount of crystalline steroid could be detected after extrusion and on storage.

Stability

Stability problems, in terms of the drug sedimentation and crystallization, encountered with nonliposomal or conventional liposome suspensions are also overcome in the current nonconventional liposome formulation. Because of the unique, cholesteryl sulfate formulations which accommodates the drug by stearic fit, and because of their high encapsulation and high retention values, drug crystallization does not occur outside or inside the liposomes, nor does sedimentation occur from the suspension. These nonconventional nonphospholipid drug containing liposomes are stable at 4° C. for up to 3 months without any evidence of the drug crystallization.

According to one aspect of the invention, the nonconventional liposome composition may be prepared and stored as a suspension, dry powder, dehydrated and as a liposome paste. These liposome formulations provide the following advantages: relatively good stability on storage, a high drug payload, a high ratio of liposome-entrapped to free drug, and very high viscosity for enhanced retention to the mucosal and ocular surface (upon reconstitution).

Methods for generating liposome pastes with up to 70% encapsulated aqueous volume have been described in co-owned U.S. patent application for "Liposome Concentrate and Method", Ser. No. 860,528 filed May 7, 1986, incorporated by reference. The concentrate is preferably formed by ultrafiltration with continued recycling of the liposome suspension material. These concentrates have equilibrium maximal loading of steroidal drugs and are stable for storage for at least three months at 4° C.

The dried particle liposome formulation in the form of dry powder can be prepared either by lyophilization or spray drying. In the former method, the small-particle suspension is quickly frozen and lyophilized or subjected to slow process lyophilization at a shelf temperature of preferably −20° C. or less.

For spray drying, the particle suspension is dried in a conventional apparatus in which the particles to be dried are sprayed in aerosolized suspension form into a stream of heated air or inert gas, and the aerosolized droplets are dried in the gas stream as they are carried toward a dry powder collector. An exemplary spray dry apparatus is a Buchi 190 Mini Spray Dryer. BBA 897:331–334 (1987). The drying temperature is between about 25°–200° C. and preferably at least about 25° C. The temperature of the collection chamber is generally lower than that of the heated air, typically about 30° C. The dried particles are collected and stored as a powder in dehydrated form, under an inert atmosphere in the presence of a desiccant. Such powders are storable under these conditions for at least a year at ambient temperature. Dry powder liposomes can be used in dry form or reconstituted or suspended in Freon propellants for aerosol administration or preferably nebulized.

Method of Preparation of Surfactant Micelles

Alternatively, steroids may be solubilized in surfactant micelles and nebulized into small aerosol particles by using appropriate nebulizers. Typical mixed micellar formulations of steroid contain an appropriate surfactant detergent such as sodium methyl cocoyl taurate (Tauranol® WS) obtained from Finetex, N.J., cholate or deoxycholate, polysorbate 20, or polyoxyethylene sorbitan monolaurate (Tween® 20) obtained from Sigma or poloxamer (Pluronic® F68 Prill) obtained from BASF Wyandotte Corp. N.J., in amount from 1–100 mg per ml, preferably between 40–60 mg/ml, mixed with steroid drug in amounts from 0.1–20 mg/ml, preferably in amount 0.2–1 mg/ml. The weight ratio of surfactant to drug is from 100–200:0.2–10, preferably around 155:1. The mixture is let stand under stirring for 2–48 hours, preferably overnight at temperature between 16°–40° C., preferably at ambient temperature. Then the mixture is filtered over filter with pore sizes smaller than steroid crystals, usually using 0.1–1$\mu$ filter. Filter, on which the undissolved drug is deposited, is discarded and the micelle filtrate is used for nebulization as described below.

Micelle is the term used to describe the suspension of surfactant in water. In a micelle-steroid drug suspension, drug is intercalated between two layers of surfactant with polar group being situated on outside. pH of micelles varies and maybe from around 4.25 to preferably around 7.4–7.8. Additionally, other additives, such as saline, mono or dibasic sodium phosphate may be added in amount to reach and/or maintain osmolality of the mixed micelles between 200–500, preferably around 300 mOsm/kg. The micelles are prepared in deionized distilled water to make up volume wherein per each ml there is present surfactant, steroidal drug, saline or other salt in amount to fall within ratios given above, preferably about 60 mg/ml surfactant; 0.4 mg/ml of drug and 9 mg/ml of saline.

While the use of micelles as particle aerosol useful for treatment of interstitial lung diseases is contemplated to be within the scope of this invention, the loading of drug into micelles and the sustained release of drug are limited.

Aerosolization or Nebulization of Liposome Formulation

Since interstitial lung diseases are primarily diseases of the deep lung, the delivery of corticosteroids and other drugs used for treatment of alveolar inflammation to the site of the inflammation is of primary interest. Focused administration of steroids or other drugs to the lung parenchyma via oral inhalation represents an attractive alternative to the oral route for the treatment of ILD and offers the potential to concentrate the drug at a site where it is needed while minimizing systemic absorption and accompanying side effects. Solubilization of steroids in an aqueous formulation and subsequent generation of small aerosol droplets by nebulization are important prerequisites toward achieving this goal. Several inhalation dosage forms of steroid drugs have been previously developed for the treatment of bronchial asthma. However, due to their inherent insolubility, steroid preparations could only be formulated as propellant suspensions, such as for example Freon 11-clathrate suspended in Freon 12/114 mixture or as aqueous suspensions with surfactants. These suspensions, which are administered by nebulization or by using propellant-based meter dose inhalation systems, are not amenable to the generation of small particle aerosols of the type required for deep lung penetration. As has been shown in the parent application, Ser. No. 284,158, filed on Dec. 14, 1988, steroids may be advantageously formulated in nonconventional i.e., nonphospholipid liposomes. Similarly, steroids may be formulated in surfactant micellar solutions. Steroids solubilized in either of these entities are able to be nebulized using appropriate nebulizers to form small particles with good drug output as described above. Nonconventional liposomes offer several advantages including greater loading efficiencies and safety. For example, nonconventional cholesterol sulfate liposome are able to incorporate around 2 mg or more of drug per ml of solution used for nebulization, generating aerosol droplets with a mass median diameter between 0.4–0.9 $\mu$. Since the size of the aerosol droplets reaching alveoli is assumed to have MMAD 0.02–2.1 $\mu$, the aerosol droplets generated by the method described below, are able to be deposited, upon inhalation, in the deep lung of alveolar tissue.

Pharmaceutical aerosols of this invention are suspensions of nonconventional liposomes or micelles containing steroid, preferably beclomethasone dipropinate in as large amounts as can be possibly formulated. For non-phospholipid liposomes, these amounts are from 0.1 mg/ml to about 2 mg/ml of suspension. For micelles, the suspended amount of steroid in surfactant, preferably Tauranol WS, is about 0.4 mg/ml.

Figure 2:
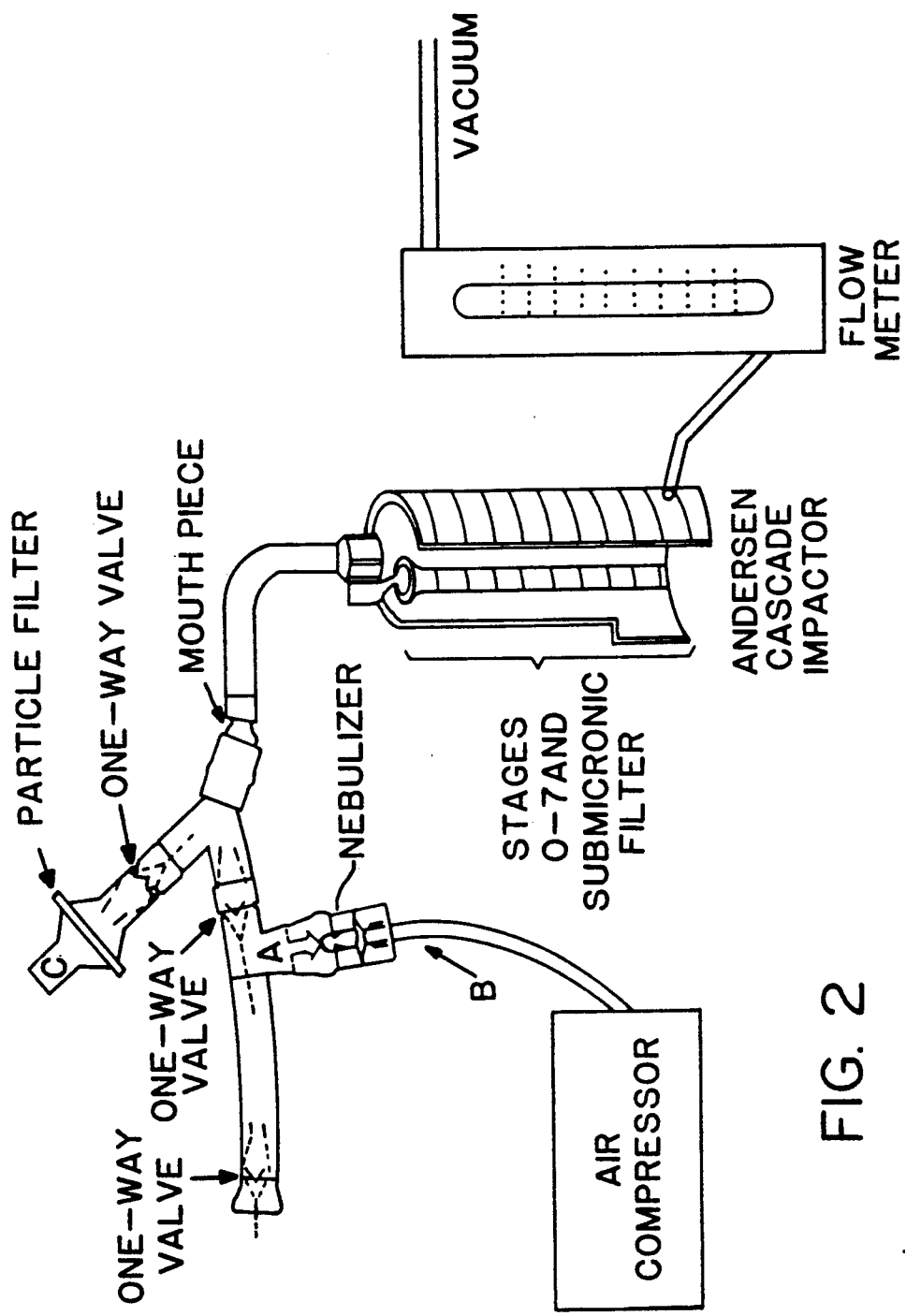
FIG. 2 is a diagram for nebulization of a steroid liposome suspension and collection of aerosol output on Anderson cascade impactor stages corresponding to the human respiratory system.

Liposomes or micelles are prepared as describe above. Liposomes are presized to contain substantially homogeneous liposome population with a mean particle size of 0.2 $\mu$. The liposomal or micellar suspension is placed in the nebulizer and, as illustrated in FIG. 2, the air compressor is attached to the lower part of the nebulizer at point B. By the pressured air generated from the compressor, the solution in the nebulizer is agitated into a mist of aerosolized particles droplets of sizes predominantly between 0.02–3 $\mu$m with an MMAD not exceeding 2.1 $\mu$m. These particles are then moved to the connecting tubing having inserted one-way valve with filter. The aerosol particles move toward the mouthpiece to be used for a patients' inhalation. Larger particles fall back to nebulizer and again undergo aerolization. In the real life situation, expired air carrying very small particles may be trapped in the air filter provided.

In practice, the nonconventional liposome steroidal suspension or micellar solution preformulated in the concentration and amount as described above (or the formulation may be sufficiently diluted with sterile saline or a suitable diluent to known concentration of active ingredient) is poured into the nebulizer, the nebulizer is connected to the air compressor, and the patient inhales via a mouth piece the aerosolized suspension.

FIG. 2 represents a model for studying a nebulization of steroid suspension on the Anderson cascade impactor stages. The principle of the model is that the impactor is divided into Stages 0–7, having segments separated from each other by the stages with pores 10 $\mu$ and above-preseparator stage, 9–10 $\mu$—Stage 0; 5.8–9 $\mu$—Stage 1; 4.7–5.8 $\mu$—Stage 2; 3.3–4.7 $\mu$—Stage 3; 2.1–3.3 $\mu$—Stage 4; 1.1–2.1 $\mu$—Stage 5; 0.65–1.1—Stage 6; and 0.43–0.65—Stage 7. A suitable filter is placed at the end to collect any submicronic droplets. As can be seen from FIG. 3, only Stages 5, 6, 7 and filter correspond to droplets of 0.4 to about 2.1 $\mu$ (MMAD) reaching alveoli. Consequently, only aerosol particles which pass Stage 4 into Stages 5, 6, 7 and submicronic filter are useful for delivering drugs into alveoli.

Figure 4:
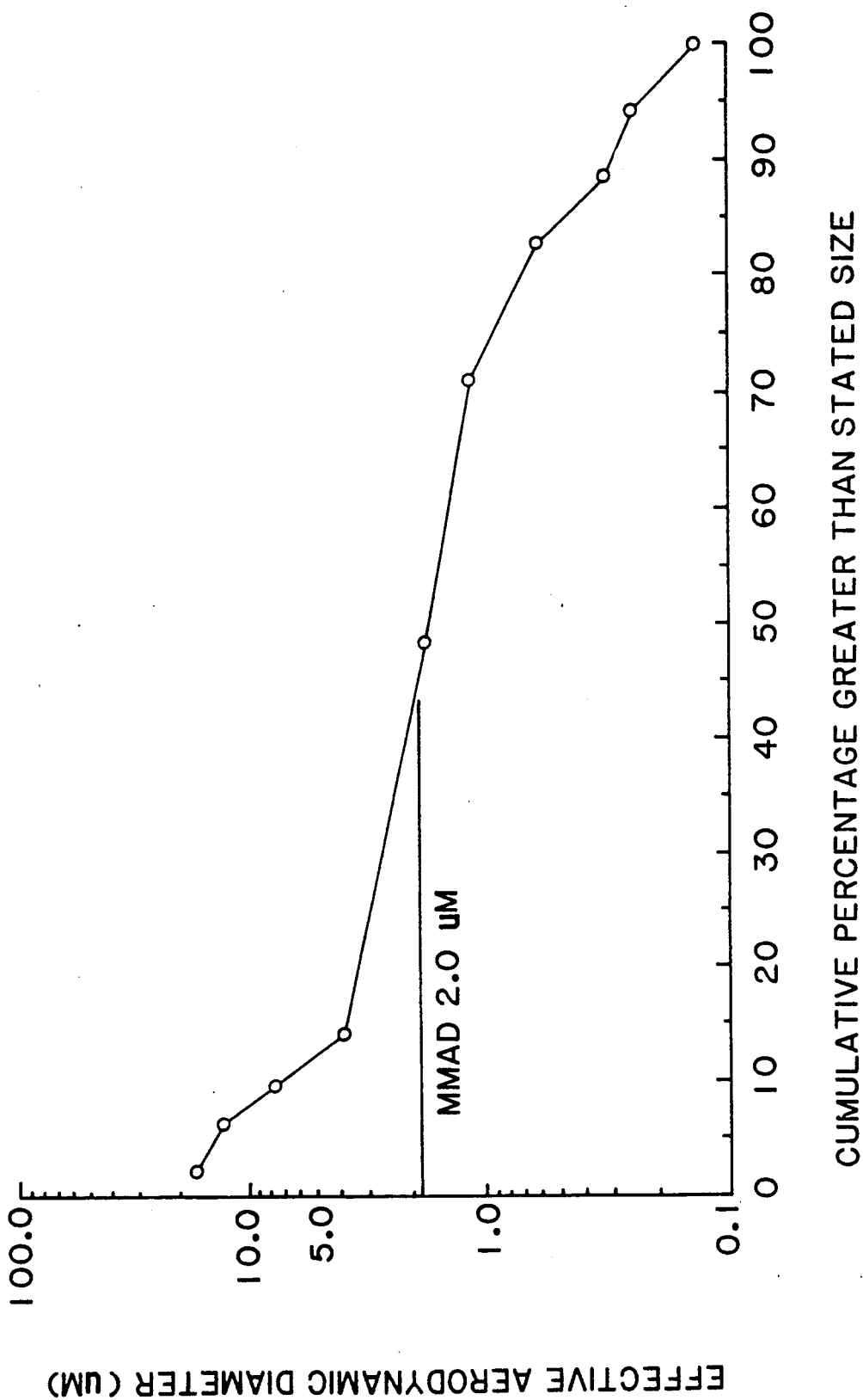
FIG. 4 shows the mass median aerodynamic diameter and aerosol particle size distribution of BECOTIDE ®.
Figure 5:
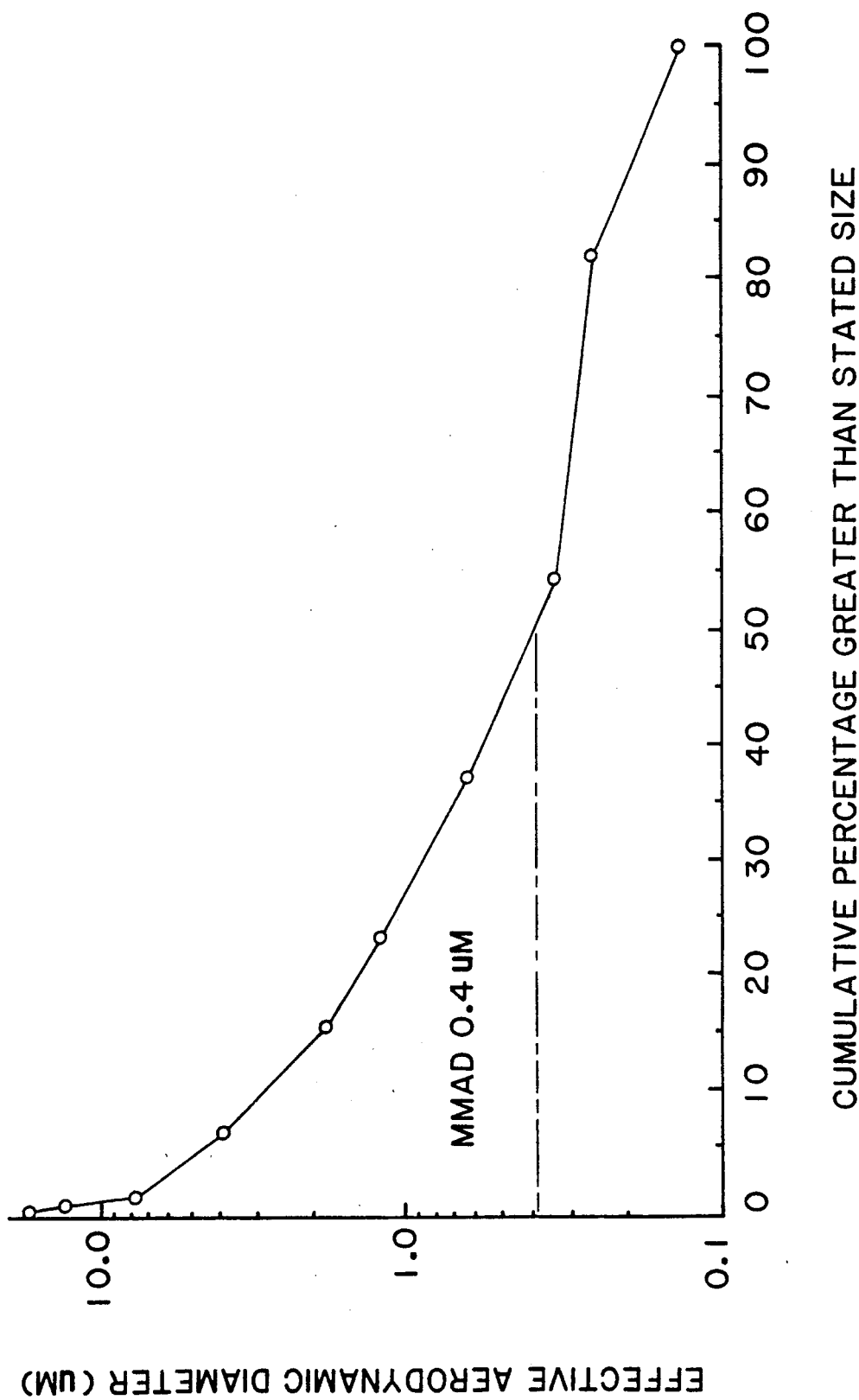
FIG. 5 shows the mass median aerodynamic diameter and aerosol particle size distribution of liposomal beclomethasone dipropionate.
Figure 6:
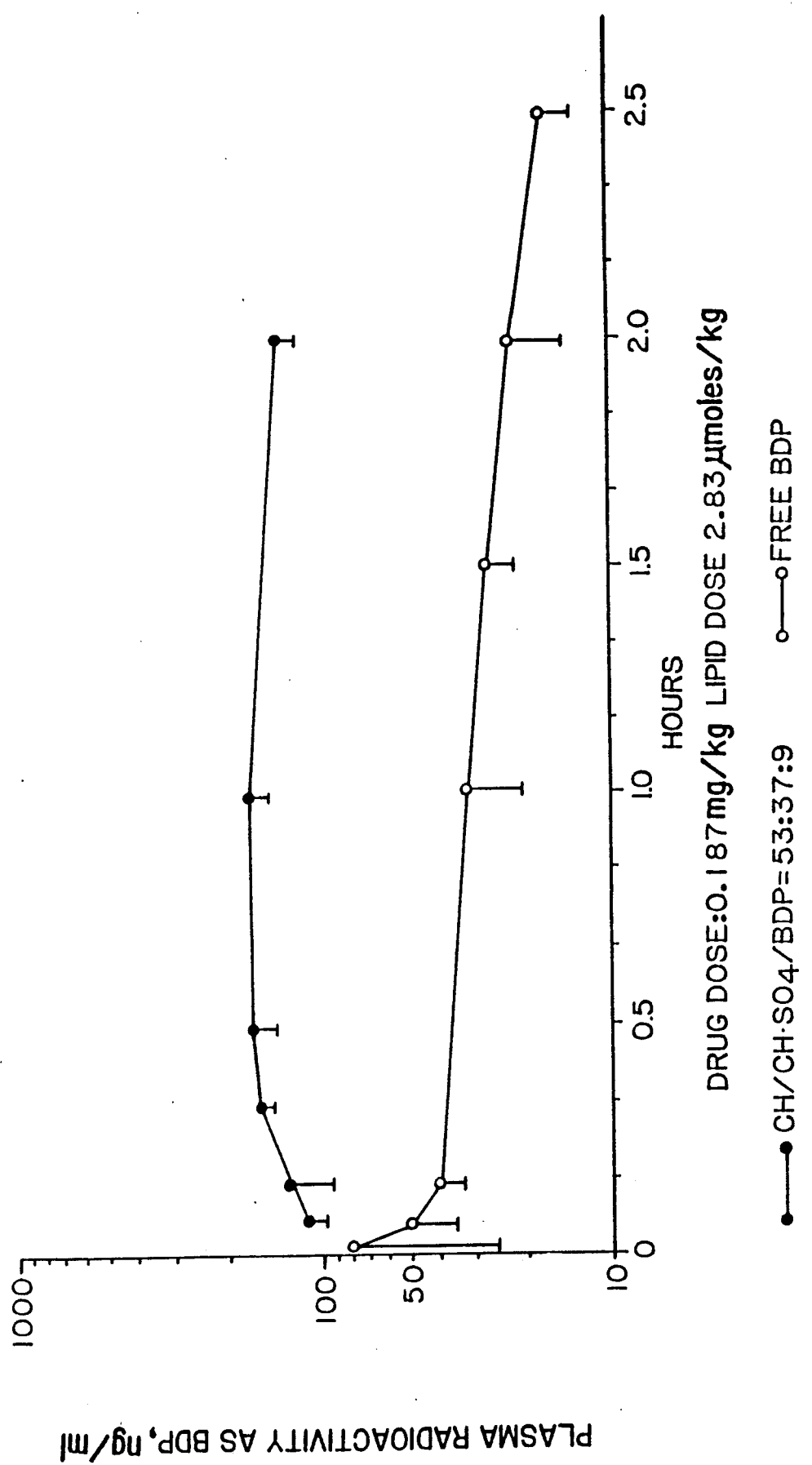
FIG. 6 shows the amount of plasma BDP radioactivity for two hours following intratracheal instillation of nonconventional liposomal BDP illustrating sustained release and for 2.5 hours following the administration of free drug.

Aerosolization of nonconventional liposomal suspension or micelles produces droplets containing the expected amount of steroid, i.e., around 1.7–2 mg/ml of aerosolized solution for liposomes and 0.4–0.5 mg/ml of aerosolized micellar solution with a mass median aerosol diameter of 0.4–0.9 $\mu$. A majority of the aerosol particles were found in stages 5, 6 and 7 of the impactor and may be delivered into alveoli. FIGS. 4 and 5 compare the alternative aqueous steroidal suspension of BECOTIDE ® (FIG. 4) to a liposomal beclomethasone dipropionate Formulation (FIG. 5).

FIG. 4 shows the liquid aerosol particle size distribution of BECOTIDE ® generated using an ultravent nebulizer with pulmoaide compressor pump mass distribution being done by QCM impactor with an isokinetic flow divider. As can be seen, 50% of all particles generated from liquid BECOTIDE ® suspension have an effective mass median aerodynamic diameter (MMAD) of 2 $\mu$. MMAD is Stokes Diameter described in *An Introduction to Experimental Aerobiology*, p. 447, Wiley (1966) and is an equivalent mean diameter. When in the same experimental set-up, the liposomes containing 2 mg/ml of beclomethasone are aerosolized, 50% of all particles have MMAD around 0.4 μ. Only 15% are larger than 2 μ, with 50% equal or smaller than 0.4 μ.

Andersen cascade impactor is obtained from Andersen Air Sampler Inc., Atlanta, Ga; QCM Cascade impactor is obtained from California Measurements, Sierra Madre, Calif. Single-use ultravent nebulizer is obtained from Mallinckrot, St. Louis, Mo., and Respigard II nebulizer is obtained from Marquest, Englewood, Colo.

Parameters followed for aerosolization were percent of drug recovery, nebulization or aerolization rate, MMAD, percent alveolar deposition relative to total nebulizer volume and analyses of fractions in nebulizer, throat, Y-joint, stages and down stream submicronic filter.

The delayed and/or sustained release of the steroid from the nonconventional liposome formulation containing combination of cholesterol/sodium cholesterol sulfate and the steroid was also studied. FIG. 6 shows the plasma radioactivity of $^{14}C$ BDP following intratracheal instillation of free $14_c$ BDP and $^{14}C$ BDP encapsulated in nonconventional liposomes. While the free BDP is quickly removed from the lungs into plasma and metabolically eliminated, the rate of release of the liposomal BDP into the plasma is much slower. The concentration of $^{14}C$ BDP in plasma initially increases, probably due to presence of some percentage of free BDP. Subsequently, it reaches and maintains certain plasma level equal to the rate of metabolic removal. In other words, after the first thirty minutes, the near equilibrium is reached in that the liposomal formulation releases only that much of the BDP into the plasma as is eliminated. Moreover, the nonconventional liposomes are able to sustain that level for measurable time. Absorption properties of the steroidal drug across lung are thus altered by drug incorporation into these liposomes.

Sustained release of four nonconventional liposome formulations, containing cholesterol sulfate/chloesterol/$^{14}C$ BDP in various ratios namely 50/40/10 mole % with 0.260 mg/kg of BDP; 55/40/5 mole% with 0.260 mg/kg of BDP; 53/37/9 mole % with 0.187 mg/kg of BDP; and 50/40/10 mole % with 0.035 mg/kg of BDP was compared with the free BDP administered intravenously and with one formulation of conventional liposomes containing cholesterol sulphate/egg phosphatidylcholine/$^{14}C$ BDP in ratio of 30/60/1.2 mole % with 0.007 mg/kg of free BDP (FIG. 7).

Linear plots were obtained when the amount of radiolabel remaining in the lungs was plotted against time on semi-log paper, indicating that all four formulations were absorbed from the lungs by a first order process. These data were fit by single exponential functions using a non-linear least squares curve fitting program (RSTRIP). The resulting slopes and intercepts were used as estimates of the absorption rate constant ($K_a$) and the amount of drug in the lungs at zero time, respectively. The absorption rate constants for the four cholesterol/cholesterol sulfate formulations ranged from $0.64^{-1}$ for ▲—▲ 0.74 $hr^{-1}$ for ■—■ 0.84 $hr^{-1}$ for ▼—▼ to 1.03 $hr^{-1}$ for ▼—▲ corresponding to an absorption half-life of 0.68 hr, 0.78 hr, 0.89 hr, to 1.09 hr, demonstrating that sustained in vivo release of liposome-incorporated BDP had been achieved. The apparently longer half-lives for free $^{14}C$ BDP (3.0 hr) and EPC/CH (2.4 hr) formulations shown in FIG. 7 are clearly not absorption half-lives since over 98% of the drug was absorbed before the first time point. These later values relate to the elimination of radiolabel already released from the liposomes and distributed to the lungs. The amount of drug in the lungs at time zero can be used to determine the amount of free drug in the formulation, since free drug is very rapidly absorbed from the lungs (Dose=free drug+amount in lungs at t=0). This amount also includes any liposome associated drug that was rapidly released ("burst⇄ effect). The amount of drug present in the lungs at time zero varied among formulations and was 90–48% for these nonconventional liposomes, although in vitro measurements by membrane exchange assay did not detect any free drug in the formulations. This would indicate that there are rapidly and slowly released pools of drug within each liposomal formulation.

The absorption kinetics (sustained release) was determined by measuring percentage of $^{14}C$ BDP remaining in the lungs following the intratracheal instillation of the above described five liposome formulations and one intravenous administration of free drug. In less than thirty minutes, 99.7% of free $^{14}C$ BDP was removed from the lungs and 98.8% of the BDP encapsulated in conventional liposomes. In contrast, only 20% of radioactivity of $^{14}C$ BDP encapsulated in the best nonconventional liposomes was removed from the lungs with 23% of radioactivity still being present at 180 minutes. The other three nonconventional liposome formulations also showed sustained release of the steroid. Thus, the presence of cholesterol in combination with cholesterol salt and the absence of phospholipids is essential for sustained release of the steroid from the nonconventional liposomes.

Corresponding plasma concentration versus time data were obtained for one of the nonconventional sustained release formulations (FIG. 6). The plasma concentration versus time curve observed after administration of $^{14}C$ BDP (0.187 mg/kg) in a cholesterol/-cholesterol sulfate liposome formulation was strikingly different from that of free drug, remaining nearly flat over the two hour duration of the study (FIG. 6).

In order to determine whether BDP was absorbed as unchanged drug or metabolized prior to release and absorption, lung samples from one study were analyzed by a thin layer chromatographic assay capable of separating BDP from its monopropionate hydrolysis products. The result showed no detectable metabolism of BDP prior to leaving the lungs.

The cholesterol ester salt and cholesterol are mandatory components of the nonconventional liposome formulation and are not interchangeable with phospholipids, normally used in conventional liposome compositions. The cholesterol is primarily responsible for, and greatly affects the sustained release, but the half life of in vivo drug-release depends on the relative amount of cholesterol sulfate and on the absolute presence of cholesterol in the composition. Drug release half life can be varied accordingly. For example, liposome composition containing egg phosphatidyl choline cholesterol sulfate: BDP (60:30:10) has a drug-release half life in vivo only slightly lower than the conventional liposomes without cholesterol sulfate or the free drug, but it has pronounced drug retention in vitro compared to compositions without cholesterol sulfate (Table IV). However, nonconventional liposome compositions containing cholesterol sulfate:cholesterol: BDP, (at a mole ratio around 50/40/10; 55/40/5; 53/37/9 mole %) gave markedly delayed release in vivo of the drug when instilled in the respiratory tract of an experimental animal and had prolonged drug retention as compared to the retention of the free drug and conventional liposomes. (FIG. 7).

Therapeutic Applications

The therapeutic applications and advantages of the aerosolizing nonconventional liposomes and micelles into small particles are numerous. Inhaled aerosolized small particles will deposit a drug encapsulated in nonconventional liposomes in the alveolar tissue in high enough amounts to allow minimal daily dosing with maximal effect extended over a period of time by sustained release. Sustained release of the drug from the nonconventional liposomes is expected to prolong the therapeutic activity after each administration, reduce the frequency of administration, further improve the ratio of localized-to-systemic effects, and provide increased and extended local therapeutic effect in the lungs.

The sustained release option is very important for successful drug delivery to alveoli. A list of factors which are known to effect a deposition of inhaled particles into deep lung include characteristics of the aerosol or its environment, characteristics of the respiratory tract structure, characteristics of the inhalant, and characteristics of the breathing pattern. *Inhalation Studies: Foundation and Techniques*, pp. 9-31 Phalen R. F. Ed. CRC Press, (1984); *New Eng. J. Med.*, 315:870 (1986). Some of these factors are listed below.

Environmental characteristics: gravitational force constant; magnetic field strength; electrical field strength; electrical ions; temperature; relative humidity; wind velocity; composition of air; barometric pressure; illumination intensity.

Inhalant and particle characteristics: geometrical size; shape; density; hygroscopicity; surface area; surface composition; electrical charge; electrical conductivity; state of agglomeration; number of particles per unit volume; temperature; irritancy, solvent.

Respiratory tract characteristics: nasal, oral, and pharyngeal anatomy; nasal hairs; electrical charge on body, nose or hairs; size and shape of laryngeal opening; tracheal anatomy; bronchial anatomy; mucus distribution; alveolar anatomy; surface temperature; surface composition.

Breathing pattern characteristics: tidal volume; air velocities; respiratory rate; functional residual capacity; air distribution among and within lobes; air-mixing characteristics; breath holding.

In one aspect of this invention spray dried or lyophilized liposomes containing steroid are diluted with 0.9% sterile saline and the suspension placed, after mixing, in a Mallinkrodt Ultravent nebulizer and the aerosol is breathed until there is no more liquid in the nebulizer. A typical volume of nebulized solution, deliverable over 10-30 minutes time period is 1-2 ml. Consequently, the ideal aerosolized liposome-steroid suspension contains from 0.2-2 mg of steroid per ml of the nebulized solution. With the loading capacity of nonconventional liposomes being around 2 mg/ml, one inhalation dosage daily is sufficient to provide a daily needed dosage of steroid for treatment of interstitial diseases of lung. However, the dosage with the same, larger or smaller amounts of the drug may be administered to a patient according to a treatment regimen prescribed by a physician.

The examples providing the data and evaluating the novel inhalation composition in this application primarily use the anti inflammatory steroid beclomethasone dipropionate (BDP), for inhalation of nebulized aerosol particles into the deep lung. The scope of the invention is not limited to BDP as a steroid.

The invention is applicable, more broadly, to all steroids related to beclomethasone, such as dexamethasone, aldosterone, betamethasone, cloprednol, cortisone, cortivazol, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortis one, meprednisone, methylprednisolone, paramethasone, prednisolone, prednisone and triamcinolone, or their respective pharmaceutically acceptable salts or esters, provided that these steroids are useful for treatment of any disease which needs or may utilize delivery to deep lung.

Moreover, in the same manner this invention is useful also for delivery of non-steroidal drugs or for mixtures of steroid and nonsteroid drugs encapsulated in nonconventional liposomes, provided that such a drug or mixture could be delivered through the lung parenchymal tissue. For example another water soluble drug could be encapsulated within these novel liposome compositions.

Examples of the classes of compounds to be used in this composition administered through inhalation therapy include, but are not limited to (1) bronchodilators, such as metaproterenol sulfate, aminophylline, terbutaline, albuterol, theophyline, ephedrine, isoproterenol, bitolterol, pirbuterol, adrenaline, norepinephrine, procaterol, and salmeterol; (2) antiinflammatory steroids, such as BDP, dexamethasone, prednisolone, hydrocortisone, fluorometholone, medrysone, fluticasone, triamcinolone, and flunisolide; (3) anticholinergics, such as atropine methyl nitrate, ipratropium bromide, (4) mast cell stabilizers, including cromolyn sodium and nedocromil, (5) cardiovascular compounds, (6) oncology drugs for treatment of lung cancer such as, bleomycine, azathioprine, doxorubicin, daunorubicin, cyclophosphomide, vincristine, etoposide, lomustine, cisplatin, procarbazine, methotrexate, mitomycin, vindesine, ifosfamide and altretamine, (7) antiviral drugs, including acyclovir, azidothymidine, ganciclovir, enviroxime, ribavarin, rimantadine and amantadine; (8) antibiotics including penicillin, erythromycin, tetracyclin, cephalothin, cefotaxime, carbenicillin, vancomycin, gentamycin, tobramycin, piperacillin, moxalactam, cefazolin, cefadroxil, cefoxitin, amikacin; (9) antifungals, including amphotericin B and micozanole (10) cardiac drugs such as antihypertensives including apresoline, atenolol, captopril, verapamil, enalapril, antiarrhytmics including dopamine and dextroamphetamine; (11) antiparasitic drugs such as pentamidine; (12) antihistamines and immunotherapeutics including pyribenzamine, chlorpheniramine, diphenhydramine, interferon, interleukin-2, monoclonal antibodies, gammaglobulin; (13) hormones such as ACTH, insulin, gonadotropin; (14) tranquilizers, sedatives and analgesics such as dilaudid, demerol, oxymorphone, hydroxyzines; and (15) vaccines hemophilus influenza, pneumococcus, HIVs and respiratory syncitial virus, alone or in combination. The liposomal composition of the invention is resilient, and can be prepared and delivered in a number of ways. For inhalation therapy, the delivery is achieved by (a) aerosolization of a dilute aqueous suspension by means of a pneumatic or ultrasonic nebulizer, (b) spraying from a self-contained atomizer using an air; solvent with suspended, dried liposomes in a powder, (c) spraying dried particles into the lungs with a propellant or (d) delivering dried liposomes as a powder aerosol using a suitable device, provided that the aerosol particles generated by any of the above means are in small size range from 0.02-2.1 μ MMAD.

The composition of the current invention has high encapsulation values, good stability, and extended shelf-life.

An added benefit to the liposome delivery system is that it can be used for combination therapy. For instance, in certain asthmatic conditions, a steroid is used for anti inflammation, while a bronchodilator is needed to relax the bronchial muscle and expand the bronchial air passages. Both can be incorporated in the nonconventional liposomes for slow release. Antibiotics, antivirals or any other water-soluble compounds can be used when dual therapy is needed to counteract the immunosuppressive characteristics of steroids.

The following examples illustrate methods of preparing nonconventional liposomes suitable for formulation of steroid drugs and using these nonconventional liposomes for treatment of interstitial lung disease. These examples are in no way intended to limit the scope of the invention.

EXAMPLE I

Preparation of Liposomes By Thin Film Hydration

This example illustrates preparation and determination of encapsulating efficiency of conventional phospholipid liposomes incorporating steroid beclomethasone dipropionate (BDP). Liposomes were formed by thin film hydration method. Unlabeled BDP obtained from Sigma was spiked with $^{14}C$-BDP. Labeled synthetic lipid dipalmitoylphosphatidyl choline $^{3}H$-DPPC (from New England Nuclear) in trace amounts was used as a lipid marker in addition to lipid determination by inorganic phosphate analysis. Conventional liposomal formulations containing steroid and phospholipid in the ratios indicated in Table 1 were prepared as follows:

A. 1 mole % of BDP spiked with $^{14}C$-BDP and 99 mole % of partially hydrogenated egg phosphatidylcholine spiked with $^{3}H$-DPPC were combined in a round bottomed flask, and dissolved in 5 ml of chloroform. The solvent was removed by a rotary evaporator at room temperature and vacuum dried for one hour under a lyophilizer. The residual thin dry lipid film was hydrated with 3 ml of phosphate buffered saline of pH 7.4 by placing the round bottomed flask on a rotary evaporator without vacuum for one hour at 30° C. and subsequently, under gentle shaking, on a mechanical shaker overnight at room temperature. The MLV's formed were heterogeneous in size between about 0.05 to 20 microns, and a predominance of multilayered structures. These liposomes were extruded through a 0.4 or a 0.2 micron polycarbonate membrane by using a stainless steel extrusion cell (Lipex Biomembrane, Inc., Vancouver, British Columbia, Canada) to produce uniform homogeneous size distribution and to remove free drug crystals (Formulation D).

B. Using the procedure of Section A, 1 mole % of BDP, 96 mole % of dilauroyl phosphatidylcholine and 3 mole % of dilauroyl phosphatidyl glycerol was formulated as formulation F.

C. Using the procedure of Section A, 10 mole % of BDP, 60 mole % of egg phosphatidylcholine and 30 mole % of sodium cholesterol sulfate was formulated as formulation H.

Table I illustrates the encapsulation values and efficiency of various conventional and nonconventional liposome formulations.

TABLE I

| Formulation[5] Mole % | Drug/Lipid Ratio Initial[1] | Drug/Lipid Ratio Final[2] | Encap. Effic. |
|---|---|---|---|
| A EPC:EPG:BDP (96:3:1.3) | 0.013 | 0.011 | 85% |
| B EPC:BDP (98:2) | 0.020 | 0.015 | 75% |
| C EPC:BDP (95:5) | 0.050 | 0.020 | 40% |
| D PHEPC:BDP (99:1) | 0.010 | 0.008 | 80% |
| E PHEPC:BDP (99:1) | 0.010 | 0.010 | 80% |
| F DLPC:DLPG:BDP[3] (96:3:1) | 0.010 | 0.010 | 100% |
| G EPC:LEPC[4]:BDP (90:8:2) | 0.020 | 0.019 | 95% |
| H EPC:CHSO4:BDP (60:30:10) | 0.100 | 0.012 | 12% |
| I CHSO4:CH:BDP (53:37:9) | 0.090 | 0.090 | 100% |
| J CHSO4:CH:BDP (50:40:10) | 0.100 | 0.100 | 100% |
| K CHSO4:CH:BDP (55:40:5) | 0.050 | 0.050 | 100% |
| L CHSO4:CH:BDP (50:40:10) | 0.100 | 0.100 | 100% |

[1]Amount formulated.
[2]After formulation and removal of non liposome associated free drug.
[3]DLPC and DLPG refer to dilauroyl phosphatides.
[4]LEPC refers to lyso egg phosphatidylcholine.
[5]All liposomes were formulated at 40 u mole/ml total lipid concentration.

Initial drug/lipid ratio refers to percent mole fraction of the drug used in the formulation. The final drug/lipid ratio means % mole fraction of drug in liposomes after formulation and removal of free drug not associated with liposomes. The encapsulation efficiency shows the amount of the steroidal drug which can be encapsulated in various nonconventional (I-L) or conventional (A-H) liposomes. As can be seen the conventional phospholipid containing liposomes can have rather high encapsulation efficiency with respect to limited amount of drug used in the formulation. But final drug/lipid ratio shows that only 2 mole % of drug could be incorporated into these liposomes at total lipid concentration of 40 u mole/ml.

Nonconventional liposome formulations prepared as described in Example III below, show high encapsulation efficiency at high drug concentration. The overall encapsulation of steroid in nonconventional liposomes was around 100% even when 10 mole % drug was used in the formulation with requirement for the amount of lipid approximately 10 times lower than for conventional liposomes.

Beclomethasone dipropionate phospholipid liposome formulations were tested for their release behavior in an in vitro exchange with membrane systems as described in Examples V and VI.

EXAMPLE II

Preparation of Liposomes by Solvent Injection Technique

This example describes the preparation of conventional liposomes using the procedure described in U.S. Pat. No. 4,235,871, A. A mixture of partially hydrogenated egg phosphatidylcholine (PHEPC IV-40, 1.98 mmol), and steroid (BDP, 0.02 mmol), in the mole ratio of 99:1 was spiked with radioactive label as in Example I.A. and dissolved in 100 ml of Freon 11 containing 1.0 ml of ethanol. Liposomal BDP dispersion was formed by slowly injecting the lipid/drug/freon solution into 50 ml of the phosphate buffered saline pH 7.4 under the following conditions: Injection rate: 1.25 ml/min; Vacuum: 400 mm Hg; Temperature: 20° C.; Mixer rate: 1000 rpm. After the injection was completed, the vacuum level was adjusted to 150 mmHg for about 30 min to remove residual solvent. Liposomes thus formed were extruded through a 0.4 or a 0.2 micron polycarbonate membrane to produce uniform size liposome distribution and to remove free drug crystals. Resulting liposomes (Formulation D, Table I) were submitted to in vitro exchange assay described in Example VI.

B. Using the procedure of Section A, 1-3 mole % of BDP, 96 mole % of egg phosphatidylcholine and 3 mole % of egg phosphatidylglycerol was formulated as formulation A.

C. Using the procedure of Section A, 10 mole % of BDP, 60 mole % of egg phosphatidylcholine and 30 mole % of cholesterol sulfate was formulated as formulation H, substituting freon with solvent alcohol/freon or alcohol/chloroform (2:1).

EXAMPLE III

Preparation of Nonconventional Liposomes

A. This example illustrates the method for preparing the nonconventional cholesterol, cholesterol sulfate containing liposomal composition for sustained release of steroids. Liposomes were prepared by a modification of BBA 691:227 (1982).

$^{14}$C-BDP used as a marker in formulations was obtained by conversion of $^{14}$C sodium propionate (1 mCi, Sp. Act. 56 mCi/mmol) to propionic anhydride which was used to acylate nonlabeled beclomethasone in the presence of acylation catalyst dimethylaminopyridine. $^3$H-cholesterol sulfate was synthesized according to a scaled-down and modified version of Mandel procedure described in *Biochem. Zeit.*, 71:186 (1915).

Steroidal drug BDP (10 mole %) and lipids sodium cholesterol sulfate (50 mole %) and cholesterol (40 mole %) in amounts (40 u mole/ml per liposomal formulation) were dissolved in 10 ml methanol:chloroform (2:1), added to a screw-cap test tube and dried under nitrogen. The procedure was repeated three times and the dried film was lyophilized for half an hour at room temperature. Depending on the liposomal volume needed, the residue was resuspended in about 2 to 5 ml of phosphate buffered saline (pH 7.4, mOsm -295, originally preserved with sodium azide) and sonicated with a bath sonicator (Model G112SPIT, 600 volts, 80 KC, 0.05 Amps) for half an hour to prepare multilamellar vesicles (MLVs). An aliquot of the sonicated, pre-extruded MLVs sample was saved and volume of preparation recorded for determination of baseline values. Liposomes were then extruded with a stainless steel Cullis high pressure extrusion cell one time through a 8.0 um Nucleopore polycarbonate membrane and two times through a 0.4 um Nucleopore polycarbonate membrane at $\leq$ 500 psi using the extrusion method described in U.S. Pat. No. 4,737,323.

A post-extrusion sample was saved to determine the amount of drug or lipid lost in the sizing process. Post-extrusion volume was noted. Free drug, if any, was removed by repeated washing with phosphate buffered saline and centrifugation. Liposomes were centrifuged three times on the Beckman L8-70M Ultracentrifuge at temperature of 4° C., at 47,600 rpm, for 1 hour, using 50 Ti rotor. The supernatant was discarded and the pellet resuspended in a volume equal to the post-extrusion volume after each centrifugation. The cleaned sample obtained by resuspending the pellet after the third centrifugation was labeled as $T_o$ sample. This sample was saved to determine percent encapsulation.

All liposome formulations I-L (Table I) were prepared according to this procedure.

B. Using the procedure outlined above, dexamethasone, hydrocortisone, prednisolone, fluoromethasone, medrysone, and all other steroids are similarly formulated in nonconventional liposomes.

EXAMPLE IV

Encapsulation Efficiency and Stability

This example illustrates lipid compositions screened by varying the level of drug BDP, determining the amount of the drug incorporated into the liposomes i.e. drug encapsulation, and monitoring the stability of drug that remains associated with liposomes over time. (Table I)

Multilamellar vesicles (MLVs) were formed containing $^{14}$C BDP in phosphate buffered saline at pH 7.4 and extruded through a 0.4 micron polycarbonate membrane as described above in Example I. The samples were washed and centrifuged several times to remove the free drug that is not associated with the liposomes according to Examples 1-3.

The vesicles were visually examined under a light microscope to detect the presence of drug crystals. No crystals were observed after encapsulation of steroidal drug (BDP) in nonconventional liposomes. Conventional liposomes had to be washed to remove the excess of the drug before they were microscopically clear of crystals. In addition BDP incorporation was low.

The level of incorporation of the drug in the liposomes was determined based on radioactive counts and expressed as encapsulation efficiency as shown in Table I.

The stability of the incorporated steroidal drug in the liposomes was followed for several days to several months. For these stability studies, liposome samples obtained above were further diluted with PBS at pH 7.4 (1:5 v/v) and incubated at ambient temperature. Time aliquots were withdrawn and pelleted by centrifugation (19,000 rpm, 4° C, 30 min). The supernatant and pellets were monitored for the presence of lipid and drug. After the liposome preparations were diluted, the amount of drug remaining in the liposomes after three days to three months was determined to assess the stability of the incorporation. Very little, if any of the steroid leaked out of the nonconventional liposomes after three days indicating that the incorporation was very stable at ambient temperature.

Nonconventional liposomes showed no crystals after three months of storage at 4° C. by light microscopy. Conventional liposomes, although appearing stable for 3 days at ambient temperature in buffer solutions, lost readily their drug content in the presence of an acceptor membrane. Conventional liposomes such as A-G (Table I) even though they showed no crystals after 3 months at 4° C. readily lost the drug content both in vitro in the presence of a membrane reservoir (Table IV) and in vivo.

Optimal composition of nonconventional liposomes containing BDP is shown in Table II. Table III list a physico-chemical characteristics of nonconventional liposomes.

TABLE II

Quantitative Composition of Non-Conventional Liposomes Containing BDP

| Ingredient | Nominal Concentration mg/ml | Assay mg/ml |
|---|---|---|
| Sodium Cholesterol Sulfate | 9.77 | N.D. |
| Cholesterol | 6.19 | N.D. |
| Beclomethasone dipropionate USP | 2.08 | 2.02 |
| Dibasic Sodium Phosphate Heptahydrate | 12.98 | |
| Monobasic Sodium Phosphate Monohydrate | 1.48 | |
| Sodium Chloride | 5.03 | |
| Deionized Water q.s to 1.0 ml | | |

Composition: Cholesterol Sulfate:Cholesterol:BDP/50:40:10 (molar ratio). Total lipid (includes drug) concentration 40 $\mu$ mol/ml.

TABLE III

| Physicochemical Characteristics of CH/CHSO$_4$/BDP | |
|---|---|
| Characteristics | Liposomes |
| Visual appearance | milky suspension |
| Odor | characteristic |
| Particle Size | 290 nm (Nicom dispersity 44%) |
| Drug Concentration | 2.0 mg/ml (UV) |
| pH | 7.4 |
| Osmolality | 290 mOsm/kg |
| Residual Solvent | <<1% (estimate) |

EXAMPLE V

In Vitro Membrane Exchange Assay

This example illustrates the sustained release or slow release in vitro from the nonconventional liposome formulations prepared according to the current invention.

An in vitro membrane exchange assay for measuring the release of drug from liposomes was established for screening the formulations before conducting bioavailability studies.

BDP, as a steroid poorly soluble in water, is primarily entrapped in the lipid bilayer rather than in the aqueous core of liposomes. Thus, based on partitioning characteristics of the drug, very little of the drug can be released into a surrounding aqueous environment unless a huge volume of buffer is used. Since BDP has good solubility in phospholipid membranes, liposomal BDP may be rapidly exchanged from the bilayer of liposomes to surrounding cell membranes in the lung. To mimic the cell membranes in the lung, an in vitro system was set up using small unilamelar vesicles (SUVs) as acceptor membranes.

An aliquot of conventional liposome formulation of BDP (EPC:EPG:$^{14}$C-BDP/96:3:1) prepared in Example I was mixed with an equal volume (50:50) containing same total molar lipid amounts of non-drug containing empty EPC SUVs' prepared according to procedure of Example I with EPC as the only lipid. Both, drug laden and empty liposomes (MLVs or SUVs), were mixed and incubated at 37°. Samples were taken at 0, 0.5, 1, 2 and 4 hours. Samples were centrifuged at 4° C. for one hour to separate the drug-containing liposomes (pellet) and the empty SUVs liposomes (supernatant). Pellets and supernatants were analyzed for radioactivity. Approximately half of all radioactivity was found in the supernatant for all time points, indicating that the drug was rapidly transferred from the drug-containing conventional liposomes to the empty SUVs until an equilibrium was reached between the two types of membranes.

Because of the rapid transfer of BDP into the SUVs, only the initial time point was used in subsequent studies. The ratio of drug-containing to non-drug containing liposomes was varied from 1:1 to 1:25. Results showed that at a ratio of 1:5 (donor/acceptor liposomes) bulk of the drug was rapidly exchanged to acceptor membranes.

This experiment was done with formulations EPC:EPG:BDP (96:3:1) and PHEPC:BDP (99:1). Both these formulations (Table IV, A and B) had a high percentage of the drug exchanged from drug containing liposomes to empty SUVs, namely 89% for EPC:EPG:BDP and 85% for PHEPC:BDP.

The same method was then used to measure the amount of drug released from three nonconventional liposome formulations of BDP (Table IV D–F) and one conventional liposome formulation containing cholesterol sulphate (Table IV C). From three nonconventional liposome formulations containing cholesterol sulfate, CH:CHSO$_4$:BDP 40:50:10; 40:55:5 and 37:53:9 mole %, none of the drug was released. Conventional phospholipid liposomes containing cholesterol 20 sulfate (EPC:CHSO$_4$:BDP/60:30:10) which were not able to incorporate more than 1.2 mole % of the drug, released 9% of the incorporated drug to the acceptor SUVs. However, these vesicles behaved like conventional liposomes types in animal models (Example VI).

From the formulations containing combination of cholesterol sulphate and cholesterol with drug, none of the drug was released into the supernatant and thus no drug was transferred between drug containing liposomes and empty liposomes and behaved as sustained or slow release steroidal drug carriers in vivo (Example VI).

TABLE IV

| Results of In Vitro Membrane Exchange Assays | |
|---|---|
| Formulation | Percent of Drug Transferred |
| A. EPC:EPG:BDP (96:3:1) | 89% |
| B. PHEPC:BDP (99:1) | 85% |
| C. EPC:CHSO$_4$:BDP (60:30:10) | 9% |
| D. CHSO$_4$:CH:BDP (50:40:10) | 0% |
| E. CHSO$_4$:CH:BDP (55:40:5) | 0% |
| F. CHSO$_4$:CH:BDP (53:37:9) | 0% |

EXAMPLE VI

In Vivo Studies

This example illustrates the in vivo studies with non-conventional liposomes and their potential for sustained release.

All studies were performed in male Sprague-Dawley rats weighing 250 to 450 g. After fasting for 16 hours, animals were anesthetized by i.m. injection of ketamine (25 mg/kg), xylazine (5 mg/kg) and acepromazine (0.5 mg/ml). During the procedure the animal's body temperature was maintained with a 37° C. heating pad. Additional anesthetic was administered as required, using half the original dose. A midline incision was made in the neck and the right jugular vein and left carotid artery were cannulated with short lengths of polyethylene tubing to which a 23 ga Luer stub adapter (Clay Adams #7565) and plastic 3-way stopcock (Argyle #173518) were attached. Blood samples (0.5-4 ml) were removed from the carotid arterial cannula after first flushing with fresh blood to clear the line. Blood volume removed was replaced with an equal volume of 5% dextrose solution containing 50 U/ml of heparin via the jugular cannula. For intravenous (i.v.) injection studies, drug was injected into the venous cannula with a 500 ul glass syringe via a 22 ga needle and injection cap and flushed with 0.5 to 1.0 ml dextrose solution.

For intratracheal (i.t.) instillation of BDP formulations, (Table V) the trachea was cannulated with a 4 cm long section of Teflon tubing (1.2 mm I.D.), inserted at the level of the fifth tracheal ring below the thyroid cartilage and tied in place with a suture. Excess fluid in the trachea was aspirated through tubing attached to a syringe. A 0.5 ml glass syringe with a blunt needle and short length of polyethylene tubing attached was used to administer the formulations. The tubing was inserted to the level of the bronchial bifurcation and the dose (100 to 400 ul) rapidly administered during an inhalation. Animals were supported head up on a tilted dorsal support (approximately 70°) during the instillation process.

Blood samples were removed at four time points during the study from each rat, centrifuged, and the serum was removed and stored frozen ($-20°$ C.) until assayed. Lung tissue samples were collected by rapidly excising the lungs after the final blood sample and immediately homogenizing in icecold acetonitrile (10.0 ml). The homogenate was briefly centrifuged and measured aliquots of the supernate removed to Teflon-stoppered glass tubes which were stored at $-20°$ C. or below until assayed.

Analysis of plasma and lung tissue samples for $^{14}$C-BDP was carried out by liquid scintillation counting. The actual dose administered in each study was determined by measurement of duplicate dose control samples of the formulation which were delivered by the same apparatus used in dosing the animals.

Nonconventional liposomes containing BDP in amounts listed in Table V were used for intratracheal instillation to Sprague-Dowley rats in order to determine their sustained release.

TABLE V

| Intratracheal Instillation to Sprague-Dawley Rats. | |
|---|---|
| Liposome Formulation (mole %) | Dose BDP (mg/kg) |
| CHSO$_4$:EPC:BDP (32.9:65.8:1.3) | 0.007 |
| CHSO$_4$:CH:BDP (53:37:9) | 0.187 |
| CHSO$_4$:CH:BDP* (50:40:10) | 0.260 |
| CHSO$_4$:CH:BDP (55:40:5) | 0.260 |
| CHSO$_4$:CH:BDP (50:40:10) | 0.035 |

*This particular composition was assessed for lung absorption at two different drug doses 0.260 and 0.035 mg/kg. In vivo "burst" effect was different in these two cases, as shown on page 31.

This formulation was prepared at 60:30:10 (molar ratio). Since BDP was incorporated only to the extent of 1.2 mole % of original amount, the ratios were adjusted accordingly.

Each of the liposomal BDP formulations shown in Table V was administered to a group of 12-18 rats as described above. Groups of 3-6 rats were sacrificed at each of three time points during each study and the amount of radiolabeled BDP remaining in the lungs was measured by liquid scintillation counting. In some studies, the plasma concentration of radiolabel was also measured over the course of the experiment.

The pharmacokinetic parameters of free BDP were determined following intravenous administration of $^{14}$C-BDP (0.008 mg/kg in 50% aqueous ethanol) to a group of 12 rats. Plasma and lung levels of radiolabel were measured as previously described. The decrease in plasma concentration versus time following free drug administration was biphasic. These data were subjected to analysis by a non-linear least squares curve fitting program (RSTRIP, MicroMath, Salt Lake City, Utah) and the resulting exponential slopes and intercepts interpreted according to a two compartment open pharmacokinetics model.

The plasma kinetics observed following the i.t. instillation of $^{14}$C-BDP (0.007 mg/kg) incorporated into EPC/cholesterol sulfate liposomes were virtually identical to those observed following the i.v. administration of a similar dose of free drug. The amount of radiolabel remaining in the lungs after 35 minutes was only 1% of the total administered dose for this formulation (FIG. 7). These data indicate that BDP is rapidly and completely absorbed from the lungs after instillation of this formulation.

The absorption kinetics of nonconventional liposomal formulations were found to differ significantly from those of free drug and formulation containing EPC and cholesterol sulfate (FIG. 7). Significant amounts of radiolabel were detected in the lungs over the course of the study for each of the four cholesterol/cholesterol sulfate formulation studied. In contrast, 98.8% of the $^{14}$C-BDP in EPC/CHS liposomes had left the lungs 30 minutes after administration and 99.7% of free $^{14}$C-BDP was absorbed in the same time period. These results demonstrate that sustained in vivo release of liposome incorporated BDP had been achieved.

Corresponding plasma concentration versus time data were obtained for one of the sustained release formulations. The plasma concentration versus time curve observed after administration of $^{14}$C-BDP (0.187 mg/kg) in a cholesterol/cholesterol sulfate liposome formulation was strikingly different from that of free drug, remaining nearly flat over the two hour duration of the study (FIG. 7). Since lung data by extrapolation indicated that 27% of the administered dose was free or rapidly released drug, the plasma concentration curve for this study reflects the sum of concentrations due to "free" and "encapsulated" drug. The concentration time curve for "free" drug was estimated by assuming 27% of the dose was immediately absorbed and followed the kinetics observed for i.v. administration of free BDP. This curve was subtracted from the experimentally observed data to give an estimate of the plasma concentration due to liposomal (sustained-release) BDP.

The present study shows that the lipophilic steroid beclomethasone dipropionate can be successfully incorporated into a nonconventional liposomal formulation that provides sustained in vivo release of the drug following intratracheal instillation.

Table VI illustrates the in vitro and the in vivo exchange of conventional and nonconventional liposomes.

TABLE VI

| Formulation | In Vitro Exchange | In Vivo Exchange |
|---|---|---|
| EPC:BDP* (98:2) | + | + |
| EPC:EPG:BDP (96:3:1) | + | + |
| EPC:CHSO4:BDP* (60:30:10) | + | + |
| CHSO4:CH:BDP (50:40:10) | − | − |
| CHSO4:CH:BDP (53:37:9) | − | − |
| CHSO4:CH:BDP (55:40:5) | − | − |

*Molar ratio of the ingredients are the starting amounts for the formulation.

EXAMPLE VII

Preformulation Studies

This example determines the localization of the steroid in the liposomal structure and illustrates the steroid's water insolubility. Beclomethasone dipropionate is a lipophilic drug. The solubility of the drug in different solvents is listed below in Table VII:

TABLE VII

| Solvent | Solubility |
|---|---|
| Ethyl Alcohol | 16.7 mg/cc |
| Chloroform | 125 mg/cc |
| Acetone | Highly soluble |
| Water | 54.4 ug/cc* |

*determined using radiolabeled material.

The partition coefficient for beclomethasone dipropionate between octanol and phosphate buffer saline was determined at pH 7.4. Nearly all (95%) of the BDP was associated with the octanol. This indicates that the drug will most likely reside in the membrane core of the bilayer.

EXAMPLE VIII

Preparation of Mixed Micelles Containing Beclomethasone Dipropionate

This example illustrates preparation of mixed micelles containing steroid beclomethasone dipropionate. 3g of Tauranol WS (60 mg/ml) is dissolved in 15 ml of deionized water and 20 mg of beclomethasone dipropionate (0.4 mg/ml) and 450 mg of sodium chloride (9 mg/ml) are added. Dionized water is added so that the volume is made up to 50 ml. The mixture is slowly stirred at room temperature overnight, then the solution is filtered through 0.2 μ filter. Filter is discarded and amount of drug, pH and osmolality of the filtrate is determined. The recovery of drug in this composition is shown as C in Table VIII. The filtrate is then poured into nebulizer vessel and nebulized to generate microaerosol particles according to Example IX. The same procedure is used but the initial amount of Tauranol is A. 750 mg (15 mg/ml) or B. 1.5 g (30 mg/ml), with 450 mg (9 mg/ml) of sodium chloride. The amount of drug is the same and the volume is made up to 50 ml. The results of drug recovery is illustrated in Table VIII.

TABLE VIII

Composition of Mixed Micelles of BDP and Tauranol WS

| Ingredients | Initial Amounts mg/ml | | | Recovered Amounts mg/ml | | |
|---|---|---|---|---|---|---|
| | A | B | C | A | B | C |
| Beclomethasone Dipropionate | 0.4 | 0.4 | 0.4 | 0.142 | 0.258 | 0.386 |
| Tauranol WS | 15 | 30 | 60 | N.D. | N.D. | N.D. |
| NaCl | 9 | 9 | 9.1 | N.D. | N.D. | N.D. |
| pH | — | — | — | 7.4 | 7.62 | 7.74 |
| Osmolality/mOsm/kg | | | | 295 | 312 | 288 |
| Deionized Distilled Water q.s. to 1 ml | | | | | | |

N.D. means not determined

As can be seen the recovered amount of beclomethasone depends on amount of surfactant detergent used and the highest recovered amount was around 98% when the 60 mg of Tauranol per ml of micelle solution was used.

Using the procedure described above, micelle solution of BDP and Tween 20 was prepared in amounts and with recovery amount shown in Table IX.

TABLE IX

Composition of Mixed Micelles of BDP and Tween ®-20

| Ingredients | Initial Amounts mg/ml | Recovered Amounts mg/ml |
|---|---|---|
| Polyoxyethylene monolaurate (Tween ® 20) | 60 | N.D. |
| BDP | 0.4 | 0.059 |
| pH | — | 4.25 |
| Osmolality | — | 321 mOsm/kg |
| NaCl | 9 | N.D |
| Deionized Distilled Water q.s. to | | 1 ml |

As can be seen the drug recovery was only approximately 15% with the same highest amount of surfactant (60 mg/ml).

Using the above procedure, micelle solution of BDP and poloxamer was prepared in amount as shown in Table X.

TABLE X

Composition of Mixed Micelles of BDP and Pluronic ® F68 Prill (A) and Pluronic ® F68 (B)

| Ingredients | A mg/ml | B mg/ml |
|---|---|---|
| Pluronic ® F68 Prill | 60 | — |
| Pluronic ® F68 | — | 60 |
| BDP (Nominal) | 0.4 mg/ml | 0.4 |
| BDP (assayed) | none | none |

The results summarized in Tables VIII-X show that not only quantity of the surfactant but also the type of surfactant is important for the amount of drug recovery in micelles. Among these three investigated, surfactant Tauranol in amount 60 mg/ml proved to be the best in terms of drug solubilization.

Michelle solutions are used for treatment of interstitial lung diseases by aerosolizing micelle solution and administering it by inhalation to a patient.

EXAMPLE IX

In Vitro Testing of Aerosolized Liposome Steroidal Formulation

This example illustrates in vitro testing of aerosolized liposome BDP formulation.

Figure 3:
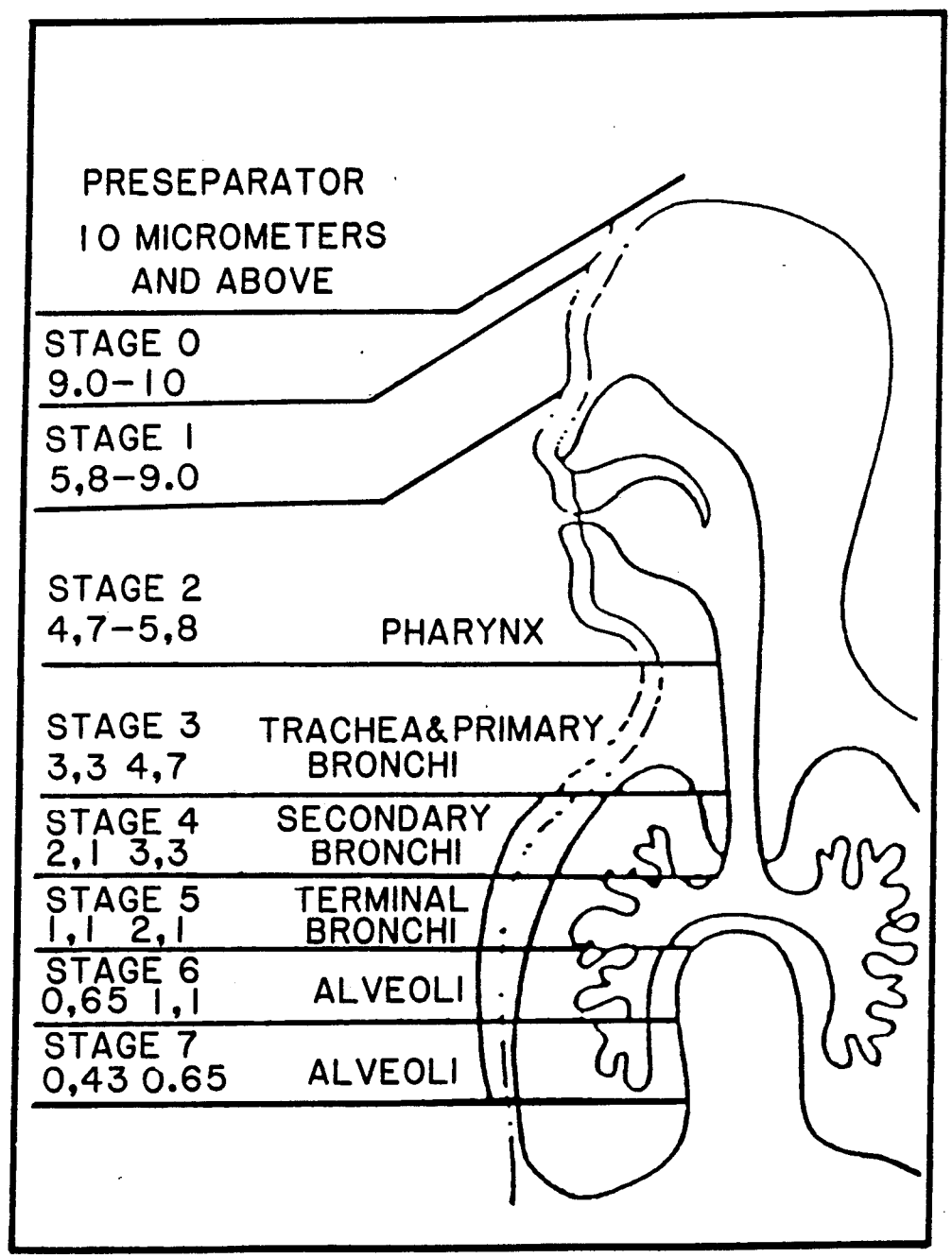
FIG. 3 depicts Andersen's Sampler as a simulator of a human respiratory, system.

4 ml of presized (0.02μ) nonphospholipid liposome (or adequate volumes of the liposome formulation to provide known amounts of drug diluted to a total volume of 4 ml with sterile saline or suitable diluent) obtained in Example 4 or mixed micelles of Example 8 containing BDP were placed in single-use Mallinkrodt Ultravent nebulizer and the compressor pump was attached according to FIG. 2. The compressed air generated by the compressor is introduced into the nebulizer and agitates the liposomal or micellar solution into mist of aerosolized particle droplets. These droplets enter via the valve into Andersen cascade impactor. The flow velocity of air through the impactor is adjusted to 28 L/minute. The aerosol mist is separated into preseparator chamber and into segments 0–7. The preseparator, and each stage of segments 0–7 are separated from each other by stages with decreasing sizes of pores. The aerosolized particles are then forced by the compressor to enter the impactor and are selectively deposited on the glass slides place on the stages when their sizes are bigger than the pores of that stage or pass through the to the next stage until they are deposited on the glass slide. The sizes of stages corresponding to various segments of the lungs are shown in FIG. 3.

After enough amount of liposomes is aerosolized, for analytical purposes (time corresponding to human breathing time in clinical trials) glass slides are removed and the content of BDP is determined spectrophotometrically after solubilization.

Experimental protocol is as follows:

Equipment (Andersen Cascade impactor) is set-up as shown in FIG. 2 after ascertaining that all sections of the equipment are clean. A blank trial is run with 4 ml of deionized water placed in the nebulizer to determine how long it takes to nebulize 1 ml. The flow meter is adjusted to allow the air flow rate of 28 l/min. 4 ml of liposome or micelle suspension (or diluted formulations in appropriate cases) is introduced into the nebulizer and nebulized to deliver approximately 1 ml of the material. Y-side arm, throat including mouthpiece, and all glass slides from stages of the impactor and submicronic aerosol filter are disconnected and removed. All of these sections where aerosol droplets have settled were rinsed separately with 5 ml of methanol/saline (0.9%) 4:1;V:V and the absorption spectrum of BDP in methanol/saline were scanned and read against standard BDP curve.

The BDP concentrations were determined spectrophotometrically for the nebulizer solutions before and after aerosolization and on the aerosol output deposited in the stages and Y-side arm. The amounts of drug (BDP) in each location was calculated and the material balance was verified as follows:

$$D_I = C_I \cdot V_I \quad D_F = C_F \cdot V_F \quad D_D = D_I \cdot D_F$$

$$D_R = D_Y + D_{S1-8} + D_{TH}$$

$D_I$ = Drug initially introduced into the nebulizer in μg or mg.
$C_I$ = Initial drug concentration in nebulizer
$V_I$ = Initial volume of solution in nebulizer
$D_F$ = Drug present in the nebulizer residue
$C_F$ = Final drug concentration in nebulizer residue
$D_D$ = Total delivered drug
$V_F$ = Final volume of solution in nebulizer
$D_R$ = Total recovered drug
$D_Y$ = Drug present in aerosol droplets deposited in the Y shaped side arm
$D_{Th}$ = Drug deposited on throat piece
$D_{S1-8}$ = Drug deposited on the seven stages and the fine or submicronic aerosol particle filter ($S_8$)

$D_F$ could be very high, implying that only water was aerosolized preferentially and "crystalline" drug remained in residue. This may very well be the case with BECOTIDE ®.

Percent recovery and aerosolization rate was calculated as follows:

$$\% \text{ recovery} = \frac{D_R \times 100}{DD}$$

$$\text{Average aerosolization rate} = \frac{V_I - V_F}{t}$$

Phospholipid concentrations are determined similarly to verify that there is a comparable material balance with lipid as well.

The drug/lipid ratio in the initial and final solutions in the nebulizer with liposomal formulations is checked. Ratio should remain constant. Any deviation points to drug crystallization and therefore unavailability for aerosolization.

Liposome particle size of the nebulization solutions are measured before and after aerosolization experiments using the NiComp laser particle sizer. Liposome particle sizes in the collected aerosol are also measured.

Typical results obtained with Cascade Impactor Analysis of commercial Becotide ® formulation and the liposomal BDP formulation are summarized in Table XI. A graphic plot of this data by standard methods gives the mass median aerodynamic diameter (MMAD) of the aerosol droplets (FIG. 4, 5). Drug/phospholipid deposition on stages and throat is used to extrapolate how much of the nebulizer output will reach "alveoli" assuming that aerosol particles of MMAD 0.02–2.1 μ can be deposited in deep lung. As seen in FIGS. 4 and 5, the Becotide suspension generates larger particles and more significantly only 3.2% of the aerosolized dose reaches stages 5, 6, 7 (Table XI) corresponding to alveolar region. On the other hand, liposomal aerosol droplets have very small size (MMAD 0.4 μ) and deliver 28% of aerosolized dose in stages 5, 6, 7 (Table XI) corresponding to alveolar region.

Results are summarized in Table XI.

TABLE XI

Andersen Cascade Impactor Analysis of Nebulized Becotide And BDP Liposomal Formulation
Volume nebulized 4 ml
HPLC Values:

| FRACTIONS | BDP (μg) Becotide ® | Liposomal BDP |
|---|---|---|
| Total | 194.4 | 979 |
| Residue | 116.7 | 604 |
| y Joint | 18.5 | 10.6 |
| Throat | 1.7 | 4.54 |
| Collar | 13.2 | 1.90 |
| Stage 0 | 0.4 | 8.95 |
| Stage 1 | 0 | 6.27 |
| Stage 2 | 0.3 | 9.87 |
| Stage 3 | 1.2 | 9.5 |
| Stage 4 | 1.2 | 16.6 |
| Stage 5 | 4.0 | 68.7 |
| Stage 6 | 1.0 | 80.0 |
| Stage 7 | 0 | 11.7 |
| Filter | 0 | 1.77 |

TABLE XI-continued

Andersen Cascade Impactor Analysis
of Nebulized Becotide And BDP Liposomal Formulation
Volume nebulized 4 ml
HPLC Values:

| FRACTIONS | BDP (μg) | |
|---|---|---|
| | Becotide ® | Liposomal BDP |
| Recovered Drug | | |
| Total: | 157.3 | 939.7 |
| Percent Recovery: | 81 | 96 |
| Alveolar Deposition: | 3.2% | 28.5% |

EXAMPLE X

Steroid Therapy in Patients Suffering from Lung Disease

This example illustrates the clinical protocol and results of treatment of patients suffering from ILD.

Very recently, several studies have implicated T lymphocytes of the inflamed lung as the source of the pathology in their release of interleukin (IL2) and T cell growth factor and their ability to continuously proliferate making lung an immune organ (Spencer, H. *Pathology of the Lung.* (1985). *New Engl. J. Med.,* 308 793 (1983), *Rev. Resoir. Dis.,* 128:634 (1983)). Active pulmonary sarcoidosis therefore, simulates a relevant model to evaluate, in humans, the invitro findings that corticosteroids can suppress the level of the lymphokine IL2 and T lymphocyte proliferation. Using bronchoalveolar lavage to sample activated T lymphocyte population, it is possible to monitor the effects of corsticosteroid formulations of the present invention in suppressing IL-2 levels (either by protein monitor using antibody or at genetic level using mRNA probes) and their ability to reduce cell proliferation in cell culture. The following experimental protocol was designed to monitor the disease course in patients with control population of normal volunteers.

Bronchoalveolar Lavage (BAL)

Prior informed consent was obtained from all individuals entering the study. Each subject was premedicated with 0.6 mg atropine sulfate i.m., 8 mg morphine sulfate and subsequently received aerosolized xylocaine (4%) and 2 puffs of Alupent ®. Bronchoscopy was accomplished with a flexible fiberoptic bronchoscope (BR-4 B/2; Olympus Corp., New Hyde Park, N.Y.) which was wedged into a subsegmental bronchus prior to BAL. Lavage was performed by an injection of warm (36° C.) saline in five 20 ml aliquots into subsegmental bronchi. Suction was applied immediately and the fluid was collected in a sterile trap. Generally volume recovered ranges from 55-70 ml. The lavage fluid was passed through 2 layers of sterile gauze and cells were pelleted at 250 g for 5 minutes and washed twice in RPM 1640 (M.A. Bioproducts, Walkersville, Md.) and then resuspended to a concentration of $10^7$; cells/ml before use.

Determination of Lung Lymphocyte Sub-populations

Monoclonal antibodies were all obtained from Becton Dickinson, Sunnyvale, Calif. T cells were identified by the monoclonal antibody Leu-4 ($CD_3$). Helper inducer T lymphocyte was recognized by monoclonal Leu-3. ($CD_4$) and Suppressor cytotoxic T subtype was identified by Leu-2 ($CD_8$). Antibodies were FITC labeled. Unstained preparations were used as control to assess auto fluorescence and non relevant mouse IgG subclasses were used as controls for nonspecific binding. Stainings were done in microtiter plates by standard methods. Because alveolar macrophages tend to clump, each sample was diluted in 400 μl of staining buffer prior to analysis. Forward light scattering was used to analyze macrophages from lymphocytes first. Limiting gates were set on lymphocyte peak.

$$\% \text{ positive cells in gated population} = \frac{\text{Positive cells}}{\text{Total cells}} \times 100$$

Percentage of Leu-4+ T cells in lymphocyte gates in patients with pulmonary sarcoid was >90%. Helper to suppressor (or $Leu3^{30}$ to $Leu2^{30}$) ratio was also evaluated. In normal volunteers this T cell subtype ratio was approximately 2 similar to the ratio in blood.

Release of IL2 by Lung Mononuclear Cells

A fraction of lung mononuclear cells at a concentration of $10^6$/ml was cultured in RPMI 1640 with 1% fetal Calf Serum for 48 hours. After this time period, supernatants were obtained by centrifugation and stored at −20°. Supernatants were assayed for the biochemical marker IL2 by their ability to stimulate $H^3$ thymidine incorporation in murine IL2 dependent CT-6 cells. Results are expressed as IL2 units by comparison with a standard. Quantitation uses profit analysis.

Analysis of Cell Proliferation

Lung lymphocyte replication was assessed by autoradiography. Lung mononuclear cells were incubated ($10^6$ cells/ml) in flat-bottom microliter wells in RPM I 1640 containing 10% heat-inactivated autologous serum and $H^3$ thymidine (0.5 μci, 2 ci/mmol, Amersham) for 24 hours. At this time, cytocentrifuge slide preparations were made of nonadherent cells. The cells were then fixed and extracted in methanol:acetic acid (3:1;v/v), developed for autoradiography with a ten day exposure and then stained with Wright-Giemsa.

$$\text{Lymphocyte labeling index} = \frac{\text{labeled lymphocyte}}{\text{total number of lymphocyte}} \times 100$$

Study design and Patient Inclusion Criteria

Study included individuals on the following criteria:
1. Diagnosis of pulmonary sarcoidosis based on lung measurements including lung biopsy or mediastinal lymph node biopsy;
2. No therapy at initial evaluation (anti-inflammatory or immune suppressive);
3. Active lymphocytic alveolitis [(BAL data showing % lymphocytes ≧30% (normal±6%); Leu $^{3+}$: Leu $^{2+}$≧2.7 (normal 2±0.3); spontaneous IL2 level≧ $5U/10^6$ lung mononuclear cells (normal OU); spontaneous proliferation of lymphocytes in 24 hour ≧4% (normal∼1%)]. Of the 21 patients included in the study, ten were treated with steroidal formulations and all individuals were monitored every month up to six months. All were monitored for pulmonary function and the biochemical markers underlying the disease namely IL2 level and spontaneous proliferation of lymphocytes collected from patients.

Results obtained with Steroid Therapy

Lung lymphocyte levels, IL2 levels, lung helper to suppressor ratio and rate of lymphocyte proliferation over 24 hours period all decreased in patients treated with the steroidal formulations as shown in the Table XII below:

TABLE XII

| Parameter Monitored | Initial Value % | Final Evaluation | |
|---|---|---|---|
| | | Untreated Group % | Treated Group % |
| Lung lymphocytes % | 52 ± 4 | 52 ± 5 | 34 ± 6% |
| Lung helper:Suppressor ratio | 2.4 ± 0.5 | 7.8 ± 1.6 | 7.4 ± 0.8 |
| Spontaneous IL2 (U/2 × $10^6$ cells) | 14.6 ± 2.6 | 12.2 ± 2.3 | 0 |
| Spontaneous T cell (% labeled nuclei) | 6.7 ± 0.4 | 5.6 ± 0.8 | <1 |

What is claimed is:

1. A nonphospholipid lipid composition for treatment of interstitial lung diseases consisting essentially of nonphospholipid lipid component and a drug, or its salt or ester, suitable for delivery by inhalation into the deep lung wherein lipid component forms lipid particles.

2. The composition of claim 1 wherein the lipid component is a mixture of cholesterol and a cholesterol ester salt and lipid particles are liposomes or micelles.

3. The composition of claim 2 wherein the cholesterol ester is selected from the group consisting of sulfate, phosphate, nitrate and maleate and the salt is selected from the group consisting of sodium, potassium, lithium, magnesium and calcium.

4. The composition of claim 3 wherein the cholesterol ester salt is sodium cholesterol sulfate.

5. The composition of claim 4 wherein the ratio of sodium cholesterol sulfate to cholesterol to the drug is from 30 to 70 mole % of sodium cholesterol sulfate; from 20 to 50 mole % of cholesterol and from 0.01 to 20 mole % of the drug or the salt or ester thereof.

6. The composition of claim 5 wherein the ratio is 50:40:10.

7. The composition of claim 5 wherein the ratio is 55:40:5.

8. The composition of claim 5 wherein the ratio is 53:37:9.

9. The composition of claim 6 wherein the drug is selected from the group consisting of aldosterone, beclomethasone, betamethasone, budesonide, cloprednol, cortisone, cortivazol, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone, triamcinolone, metaproterenol sulfate, aminophylline, terbutaline, albuterol, theophyline, ephedrine, isoproterenol, bitolterol, pirbuterol, adrenaline, norepinephrine, procaterol, salmeterol, fluoromethasone, medrysone, fluticasone, atropine methyl nitrate, ipratropium bromide, cromolyn sodium, nedocromil, bleomycine, azathioprine, doxorubicin, daunorubicin, cyclophosphomide, vincristine, etoposide, lomustine, cisplatin, procarbazine, methotrexate, mitomycin, vindesine, ifosfamide, altretamine, acyclovir, azidothymidine, ganciclovir, enviroxime, ribavarin, rimantadine, amantadine, penicillin, erythromycin, tetracyclin, cephalothin, cefotaxime, carbenicillin, vancomycin, gentamycin, tobramycin, piperacillin, moxalactam, cefazolin, cefadroxil, cefoxitin, amikacin, amphotericin B, micozanole, apresoline, atenolol, captopril, verapamil, enalapril, dopamine, dextroamphetamine, pentamidine, pyribenzamine, chlorpheniramine, diphenhydramine, interferon, interleukin-2, monoclonal antibodies, gammaglobulin, ACTH, insulin, gonadotropin, dilaudid, demerol, oxymorphone, hydroxyzines, hemophilus influenza vaccine, pneumococcus vaccine, HIV vaccine and respiratory syncitial virus vaccine or their respective pharmaceutically acceptable salts or esters, alone or in combination.

10. The composition of claim 9 wherein the drug is beclomethasone dipropionate.

11. The composition of claim 10 wherein the composition is aerosolized into particles predominantly smaller than mass median aerodynamic diameter 2.$\mu$.

12. The composition of claim 11 wherein beclomethasone dipropionate is present in amount between 0.4 to 2 mg/ml of liposome composition.

13. A method of treating interstitial lung diseases by inhalation route of administration to a person in need of such treatment a therapeutically effective amount of nonphospholipid lipid composition consisting essentially of a drug and nonphospholipid lipid components aerosolized into aerosol particles having mass median aerodynamic diameter smaller than 2.1 micron and providing a slow or sustained release of the drug in the lung.

14. The method of claim 12 wherein the lipid composition forms liposome or micelle lipid particles comprising 30 to 70 mole % of sodium cholesterol sulfate, 20 to 50 mole % of cholesterol and from 0.01 to 20 mole % of a drug.

15. The method of claim 13 wherein the drug is selected from the group consisting of aldosterone, beclomethasone, betamethasone, budesonide, cloprednol, cortisone, cortivazol, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone, triamcinolone, metaproterenol sulfate, aminophylline, terbutaline, albuterol, theophyline, ephedrine, isoproterenol, bitolterol, pirbuterol, adrenaline, norepinephrine, procaterol, salmeterol, fluoromethasone, medrysone, fluticasone, atropine methyl nitrate, ipratropium bromide, cromolyn sodium, nedocromil, bleomycine, azathioprine, doxorubicin, daunorubicin, cyclophosphomide, vincristine, etoposide, lomustine, cisplatin, procarbazine, methotrexate, mitomycin, vindesine, ifosfamide, altretamine, acyclovir, azidothymidine, ganciclovir, enviroxime, ribavarin, rimantadine, amantadine, penicillin, erythromycin, tetracyclin, cephalothin, cefotaxime, carbenicillin, vancomycin, gentamycin, tobramycin, piperacillin, moxalactam, cefazolin, cefadroxil, cefoxitin, amikacin, amphotericin B, micozanole, apresoline, atenolol, captopril, verapamil, enalapril, dopamine, dextroamphetamine, pentamidine, pyribenzamine, chlorpheniramine, diphenhydramine, interferon, interleukin-2, monoclonal antibodies, gammaglobulin, ACTH, insulin, gonadotropin, dilaudid, demerol, oxymorphone, hydroxyzines, hemophilus influenza vaccine, pneumococcus vaccine, HIV vaccine and respiratory syncitial virus vaccine or their respective pharmaceutically acceptable salts or esters, alone or in combination.

16. The method of claim 14, wherein the composition is 50 mole % of sodium cholesterol sulfate, 40 mole % of cholesterol and 10 mole % of beclomethasone dipropionate.

17. The method of claim 14, wherein beclomethasone dipropionate is present in amount from 0.4 to 2 mg/ml of liposome composition.

18. An inhalation method for treatment of lung diseases by treating a person in need of such treatment with a therapeutically effective amount of aerosolized liposome composition consisting essentially of a drug and nonphospholipid lipid components aerosolized into particles predominantly smaller than 1 micron mass median aerodynamic diameter by the inhalation route of administration.

19. The method of claim 17 wherein the lipid composition forms liposome or micelle particles comprising 30 to 70 mole % of cholesterol sulfate, 20 to 50 mole % of cholesterol and 0.01 to 20 mole % of the drug.

20. The method of claim 18 wherein the drug is selected from the group consisting of aldosterone, beclomethasone, betamethasone, budesonide, cloprednol, cortisone, cortivazol, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone, triamcinolone, metaproterenol sulfate, aminophylline, terbutaline, albuterol, theophyline, ephedrine, isoproterenol, bitolterol, pirbuterol, adrenaline, norepinephrine, procaterol, salmeterol, fluoromethasone, medrysone, fluticasone, atropine methyl nitrate, ipratropium bromide, cromolyn sodium, nedocromil, bleomycine, azathioprine, doxorubicin, daunorubicin, cyclophosphomide, vincristine, etoposide, lomustine, cisplatin, procarbazine, methotrexate, mitomycin, vindesine, ifosfamide, altretamine, acyclovir, azidothymidine, ganciclovir, enviroxime, ribavarin, rimantadine, amantadine, penicillin, erythromycin, tetracyclin, cephalothin, cefotaxime, carbenicillin, vancomycin, gentamycin, tobramycin, piperacillin, moxalactam, cefazolin, cefadroxil, cefoxitin, amikacin, amphotericin B, micozanole, apresoline, atenolol, captopril, verapamil, enalapril, dopamine, dextroamphetamine, pentamidine, pyribenzamine, chlorpheniramine, diphenhydramine, interferon, interleukin-2, monoclonal antibodies, gammaglobulin, ACTH, insulin, gonadotropin, dilaudid, demerol, oxymorphone, hydroxyzines, hemophilus influenza vaccine, pneumococcus vaccine, HIV vaccine and respiratory syncitial virus vaccine or their respective pharmaceutically acceptable salts or esters, alone or in combination.

21. The method of claim 19, wherein the composition is 50 mole % of sodium cholesterol sulfate, 40 mole % of cholesterol and 10 mole % of beclomethasone dipropionate.

22. The method of claim 19, wherein beclomethasone is present in amount from 0.4-2 mg/ml.

23. A process of preparing a suspension of nebulized aerosol particles of sizes predominantly smaller than 2.1 microns of nonphospholipid lipid particles comprising:
(a) preparing a nonphospholipid lipid particles having sizes less than 1 micron in an aqueous suspension; and
(b) nebulizing suspension under conditions which produce aerosol particles of mass median aerodynamic diameter predominantly smaller than 2.1 microns.

24. The process of claim 23 wherein the lipid particle is liposome.

25. The process of claim 23 wherein the lipid particle is micelle.

26. The process of claim 23 wherein the nebulizer is any nebulizer suitable for the generation of particle aerosols predominantly smaller than 2.1 microns mass median aerodynamic diameter.

27. A nonphospholipid micelle composition for treatment of interstitial lung diseases consisting essentially of nonphospholipid lipid components and a drug or its salt or ester, suitable for delivery by inhalation into the deep lung.

28. A nonphospholipid liposome composition for treatment of interstitial lung diseases consisting essentially of nonphospholipid lipid components and a drug or its salt or ester, suitable for delivery by inhalation into the deep lung wherein liposome sizes are predominantly not larger than 1.0 microns.

* * * * *